United States Patent [19]

Summer et al.

[11] Patent Number: 5,730,151
[45] Date of Patent: Mar. 24, 1998

[54] TOOTH CONTACT SENSING APPARATUS AND METHOD

[75] Inventors: John D. Summer, 833 S.W 11th Ave. #810, Portland, Oreg. 97205; Edmund Pierzchala, Milwaukie; Marek Perkowski, Beaverton, both of Oreg.

[73] Assignee: John D. Summer, Portland, Oreg.

[21] Appl. No.: 671,932

Related U.S. Application Data

[60] Provisional application No. 60/000,758, Jun. 30, 1995.

[22] Filed: Jun. 27, 1996
[51] Int. Cl.⁶ ................................................. A61B 5/10
[52] U.S. Cl. ................................................. 128/777
[58] Field of Search ................................. 128/777

[56] References Cited

U.S. PATENT DOCUMENTS

| | | |
|---|---|---|
| 4,629,424 | 12/1986 | Lauks et al. .................. 128/777 |
| 4,788,987 | 12/1988 | Nickel . | |
| 4,842,519 | 6/1989 | Dworkin ........................ 128/777 |
| 4,859,181 | 8/1989 | Neumeyer . | |

*Primary Examiner*—William E. Kamm
*Attorney, Agent, or Firm*—Klarquist Sparkman Campbell Leigh & Whinston

[57] ABSTRACT

An apparatus and method for sensing tooth contact includes at least one, and more typically plural, vibration sensors which are coupled to the non-biting surfaces of teeth. These sensors produce output signals when the associated teeth contact one another during jaw closing, the output signals being processed to provide information concerning tooth contact. For example, information concerning the first tooth which contacts may be determined, the sequence of contact by various teeth may be determined, as well as the time between contact of the various teeth. Other information concerning tooth contact may also be determined and displayed in a variety of forms. The device may be implemented in circuit as well as in microprocessor forms. In addition, in combination with a jaw trajectory apparatus, the tooth contact information may be correlated with jaw trajectory information to provide a more complete indication of the stability of a patient's bite.

47 Claims, 18 Drawing Sheets

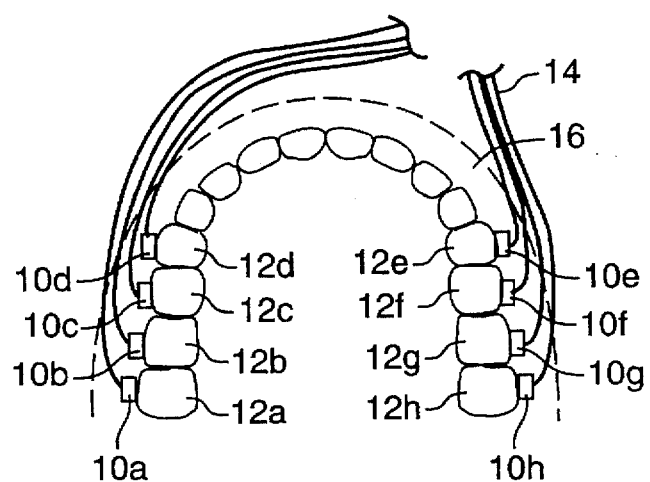
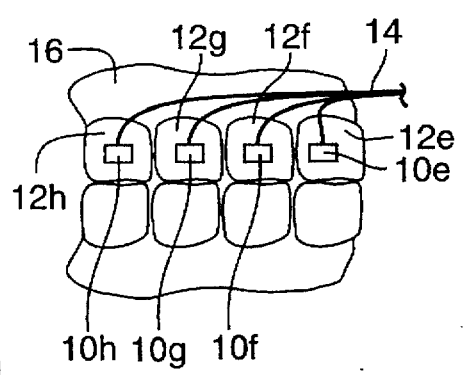
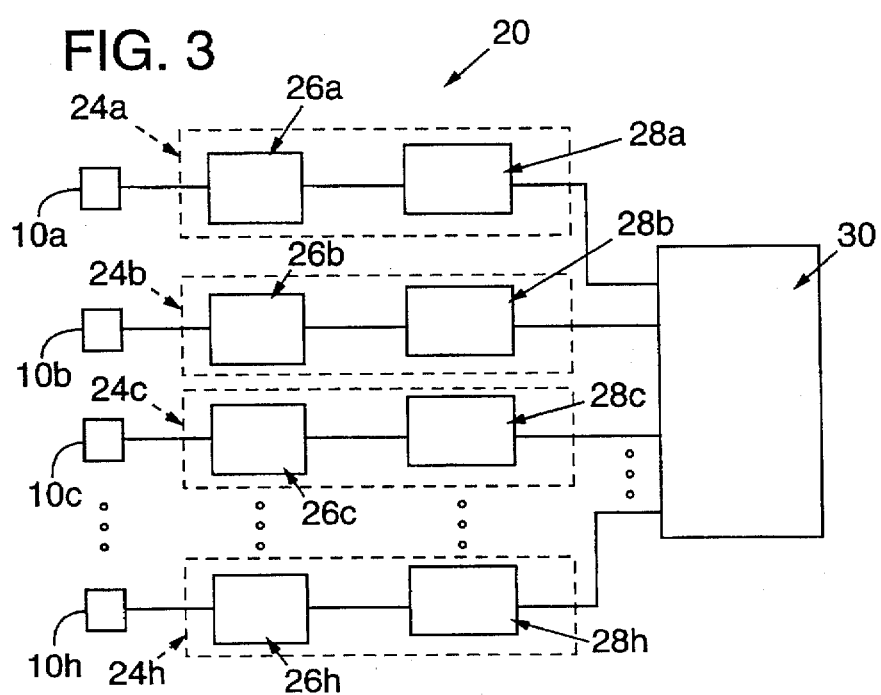

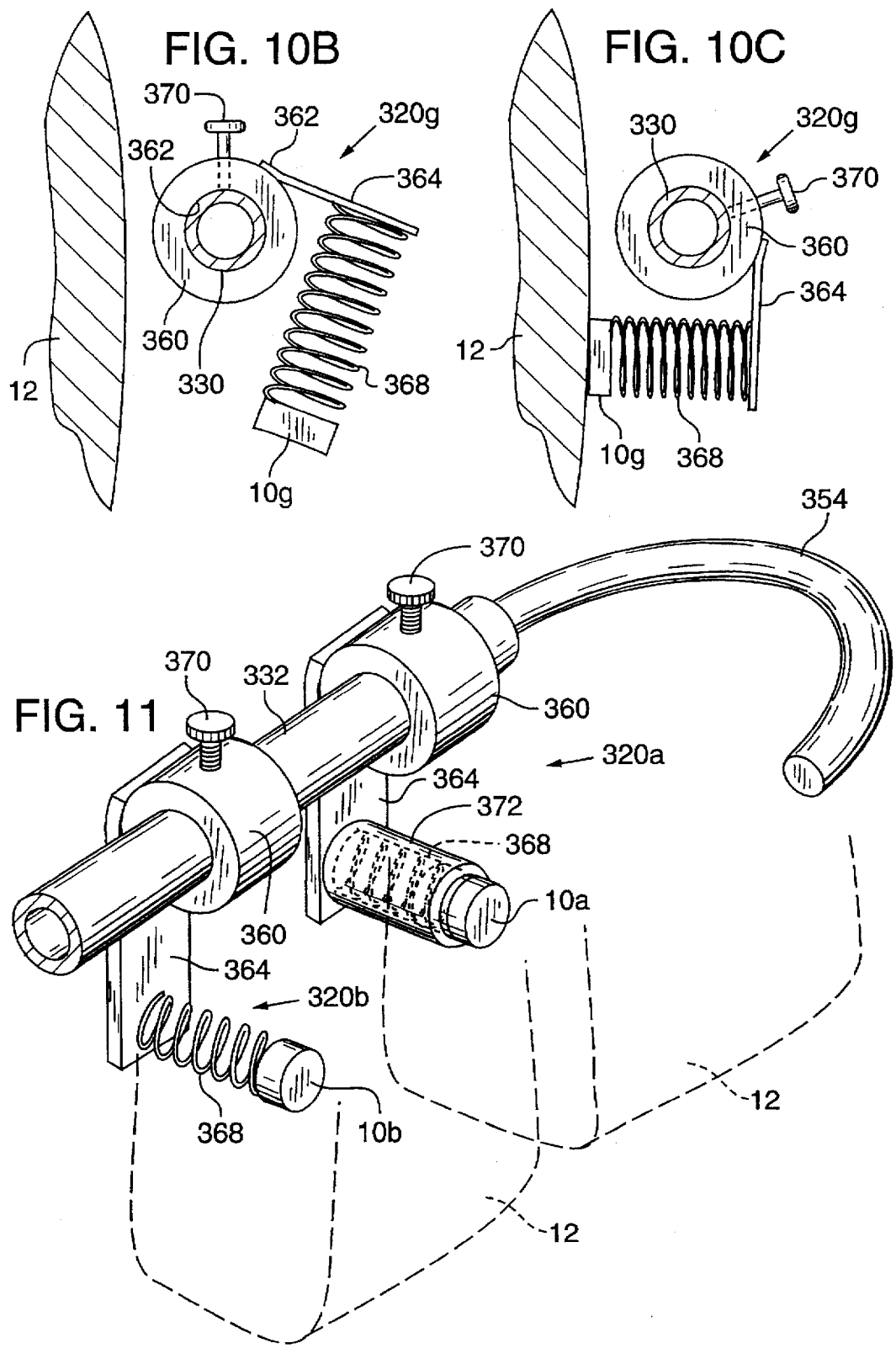

FIG. 17

LED "ON"
LED "OFF"

TOOTH CONTACT SENSING APPARATUS AND METHOD

REFERENCE TO PRIOR APPLICATION

This application claims the benefit of U.S. Provisional Application No. 60/000,758 filed Jun. 30, 1995 now abandoned. This provisional application was entitled TOOTH CONTACT SENSING APPARATUS AND METHOD.

BACKGROUND OF THE INVENTION

The present invention relates to detecting premature tooth contacts during closing of an individual's jaw. This information may be used in evaluating and treating an unstable bite to bring occlusal equilibrium.

Dentistry has long been aware of the importance of creating a bite in which all the teeth contact simultaneously when the jaw is closed. However, many dental patients, especially those suffering from temporomandibular joint (TMJ) problems, lack such bite stability. In a process called occlusal equilibration, dentists frequently attempt to recreate bite stability by repeatedly shaving down the top surface of the tooth or teeth that contact first until all the teeth contact simultaneously.

One difficulty in performing this process arises from the lack of a reliable approach for determining the first or premature tooth contact, let alone information on tooth contact in general, such as the sequence and timing between contacts. A number of prior art techniques have been tried over the years in an attempt to detect premature tooth contacts.

One common approach, which is still practiced, involves using thin pieces of carbon paper or wax placed between the teeth so that the biting surfaces of the teeth engage the inserted material during biting and leave some visible mark or indentation. However, even the thinnest marking paper available, when placed between the teeth, slightly changes the bite by its thickness. The thinnest marking substances produced are about eight microns thick. This thickness is enough to leave a tooth eight microns higher than adjacent teeth during biting, a clinically significant difference in many cases. Another problem with techniques utilizing a marking material is that, when the neuromusculature detects a substance between the teeth, it frequently changes the trajectory of the jaw closure to accommodate the substance. When the jaw trajectory changes, accurate determination of premature tooth contact becomes virtually impossible. Another contributing factor to the inaccuracies of marking substance approaches is that teeth move several microns in their sockets very easily, for example during biting. Consequently, the first tooth that is contacted shifts in its socket until the next tooth contact is struck, and, in such a case, marking materials provide no means to distinguish between which of the two teeth contacted first.

Recently, additional disclosures have been made of approaches which employ various types of sensors placed between the biting surfaces of the teeth for the purpose of detecting tooth contact. U.S. Pat. No. 4,488,873 to Bloomfield et al.; U.S. Pat. No. 4,592,727 to Bloomfield et al.; U.S. Pat. No. 4,521,186 to Wodlinger et al.; and U.S. Pat. No. 4,856,993 to Maness are understood to be examples of approaches wherein a wafer or other device is placed between the teeth to detect tooth contact by deforming in response to pressure from teeth during biting. These approaches suffer from a number of the same drawbacks as the carbon paper marking techniques explained above.

Dentists also need a means to measure the stability of a patent's bite, i.e. the relative simultaneity of their tooth contacts during closing. Currently, this is done either by a carbon paper technique or by judging the sharpness of the sound heard by a dentist and made as a patient closes his or her mouth. Both of these approaches are not reliable.

Therefore, a need exists for an improved method and apparatus for detecting premature tooth contact, measuring occlusal stability, and acquiring other information relating to the contact or engagement of teeth during biting.

SUMMARY OF THE INVENTION

In determining the contact between at least one set of two teeth, each set including an upper tooth and a lower tooth which contact one another at respective biting surfaces, a sensor is coupled to a non-biting surface of a first tooth of the set. The sensor produces an output signal upon contact between the two teeth. The output signal is processed by a signal processor to indicate the contact of the two teeth.

As teeth contact, they vibrate as well as move within their socket. The sensor broadly includes any sensor capable of detecting this movement without being positioned between the biting surfaces of the contacting teeth. The sensor preferably comprises a shock pulse or vibration sensor and in the most preferred form comprises an accelerometer. A small piezoelectric accelerometer is particularly advantageous.

The sensor may be mounted to the upper or lower tooth of the set, but in most people is preferably mounted on the upper tooth. On occasion, sensors may be mounted to both the upper and the lower teeth of sets of teeth, as two upper teeth may be contacted by a single lower tooth, and similarly two lower teeth may be contacted by an upper tooth By including plural upper and lower sensors, it is possible to determine which of the two contacting points on a single tooth is striking first. In a typical application plural sensors are utilized, for example, four, six or eight or more sensors (for example 16 sensors, one coupled to each upper tooth) coupled to teeth, such as the upper teeth. Signals from these sensors may be processed to gain additional information about the teeth. For example, the sequence of contact of the various teeth may be determined in addition to, or instead of, determining the first teeth to contact. Also, the degree to which a bite is unstable may be determined by measuring the time between successive teeth contacts or required for all tooth contacts to occur.

The sensors are preferably enclosed in a liquid impermeable sterilizable housing so that the sensors may be sterilized and reused following the evaluation of the bite of a particular patient.

Additionally, the sensors may be coupled to the non-biting surfaces of the teeth by any suitable mechanism. For example, a sensor, with or without a retentive backing, may be temporarily glued or otherwise temporarily directly and rigidly affixed to the appropriate tooth surface. As another option, the sensors may be embedded in a polyvinylsiloxane or other matrix formed to fit in a patient's mouth with the sensors held by the matrix against the patient's teeth. As a further option, a mounting bracket may be detachably secured to the tooth surface, with the sensor being detachably coupled to the mounting bracket and thereby indirectly coupled to the tooth.

As yet another approach, the sensors may be supported by a bite fork or other support in a patient's mouth, slid into position in the user's mouth, and held against the respective teeth for the purposes of detecting tooth contact. A biasing mechanism, such as springs, pneumatic pressure, or hydraulic pressure may be used for biasing the sensors against the teeth.

In one specific form, the bite fork comprises a spring biased tong-like structure with sensors slidably coupled to the body of the bite fork. When one end portion of the bite fork is inserted into the user's mouth and secured temporarily in place, the sensors may be slid along the bite fork and temporarily secured, for example by a set screw, at the desired position. The sensors in this case may be spring-biased to bear against the associated tooth surface to which the sensor is coupled.

The bite fork may include a retainer, such as a bendable wire, for engaging the two rear most upper teeth of a patient to rigidly and temporarily secure the bite fork in a supported position within the patient's mouth. The tongue or handle portion of the bite fork extends from the user's mouth and may be supported, for example, from temporary eye glasses worn by the user, to provide support at the front of the bite fork. Thus, stable support is provided to the sensors coupled to the bite fork.

As yet another optional aspect of the bite fork, the portions of the bite fork inserted into the user's mouth may be of a bendable material, such as copper tubing, and detachably coupled to the tong or handle portion of the bite fork. The bendable portions may be bent or shaped during use to better fit the contour of a user's mouth. Such bendable portions may be readily detached from the handle portion of the bite fork and discarded. New bendable portions, for example of different lengths for patients with dental arches of deficient lengths, being attached to the handles for use with a subsequent patient. The bite fork may be used to support other types of sensors and dental devices, as well as for supporting vibration sensors.

To again indicate the wide variety of suitable sensor supporting approaches, the sensor carrier may be in an arch shaped configuration and of any suitable material,.such as of plastic, or of a bendable wire (such as piano wire). In the case of a wire, the wire may be bent to conform to the patient's dental arch. Sensors, such as described above, may be slidably or otherwise coupled to the carrier and held in position against the patient's teeth. In this case, nothing projects from the patient's mouth other than wires connected to the sensors if electrical signal generating sensors are used. The sensors may be biased against the teeth, e.g. by a biasing spring. Vibration dampening may be accomplished by using a resilient carrier or other dampening mechanism so that vibrations from other teeth and from movement of the sensor support structure are dampened at least in part before reaching the sensor.

The signal processing circuit may include a display which is operable to visually indicate the contact between teeth. In addition, where plural sensors are used, the visual display may indicate the sequence of contact between teeth as well as other information. A computer monitor may, for example, be used to provide such a visual display. In addition, the information may be simply stored for subsequent use and/or reviewed by a dentist or other professional. Also, peripheral devices may be utilized, such as printers, to provide a tangible copy of the processed signals. Furthermore, although less usable than visual displays, auditory indications may be provided to indicate tooth contact.

In one illustrated embodiment, a signal processing circuit is provided with a respective channel coupled to each sensor. The channel includes an amplifier, a band pass or low pass filter, and a comparator for determining when the magnitude of the output signal produced by tooth contact exceeds a threshold magnitude and is thus considered to be a reliable indicator of tooth contact. These circuit components may be varied. Any suitable circuit may be used which provides a usable signal corresponding to a sensor having detected tooth contact.

The signal processing circuit in one specific form may include a plurality of storage devices for storing signals indicating the sequence of contact of the sets of teeth. These storage devices may, for example, comprise shift registers. In one simple form of visual display, the signal processing circuit may include a plurality of light emitting diodes to visually indicate the contact of and/or the sequence of contact of teeth.

In a computerized version of the present invention, tooth contact information may be displayed in a variety of manners. For example, an average of the results of a plurality of taps of a patient's jaw, indicating tooth contact associated with the taps, may be provided. The sequence of contact by the teeth may also be displayed. The tooth contact data may be presented in other ways, such as the percentage of the time each tooth is contacted first, second and third, for example. In addition, a graphical display of a tooth containing jaw may be provided with information overlaid on the graphical display to indicate which tooth contacted first, the order of contact of the different teeth, shading indicating the frequency particular teeth contacted first or in some other sequence, as well as other information such as the timing between the contact between different sets of teeth.

As another specific example of a signal processing circuit, a signal shaping circuit may be provided having plural signal shaping channels. Each signal shaping channel is coupled to an associated sensor for receiving the output signal from the associated sensor upon contact of the teeth with which the sensor is associated. Each signal shaping channel may include a band pass or low pass filter, an amplifier and a threshold comparator. The signal shaping channels each provide a shaped output signal at a first logic level in response to an input signal which corresponds to the associated sensor detecting contact between the associated set of teeth. A digital signal processing circuit comprising plural state indicating channels may also be provided. The state indicating channels are coupled to a respective associated signal shaping channels. In this specific embodiment, the digital signal processing circuit may include at least one state storage circuit in each state indicating channel. The state storage circuit stores a tooth contact indicating state in response to a shaped output signal at the first logic level from the associated signal shaping channel. A visual display coupled to the digital signal processing circuit is operable to visually indicate the status of the state storage circuits in a tooth contact indicating state.

In addition, each state indicating channel may include plural state storage circuits connected in series and responsive to a clock operating at a clock frequency. In this embodiment, a first state storage circuit of a first state indicating channel is triggered to a tooth contact indicating state in response to a shaped output signal at the first logic level from an associated first signal shaping channel. The digital processing circuit is operable to maintain the status of the state storage circuit constant until a clock edge occurs when a shaped output signal at the first logic level is present from another signal shaping channel. A first state storage circuit of another state indicating channel is then triggered to a tooth contact indicating state in response to the shaped output signal at the first logic level from the other signal shaping channel. In addition, the first state storage circuit of the first state indicating channel continues to indicate tooth contact. The visual display in this case may then be operable to display the sequence of contact by the sets of teeth as well as, or instead of, the first teeth which contact.

In a general case, N sensors are provided (for example eight sensors or more) with N state indicating channels. In such a case, the state storage circuits of each channel may comprise a shift register including N bits. A first bit of the shift register of one state indicating channel is triggered to a tooth contact indicating state in response to the delivery of a shaped output signal at the first logic level to said one state indicating channel. In addition, the other bits of the shift register of said first state indicating channel are successively triggered to a tooth contact indicating state in response to the delivery of a shaped output signal at the first logic level to the other state indicating channels. In addition, the visual display may comprise a matrix of light emitting diodes each coupled to a respective bit of the shift registers and indicating when the coupled shift register bit is in a tooth contact indicating state.

Much of this circuitry may be eliminated in a computer or microprocessor version of the present invention, as processing in large part may be performed by the microprocessor or computer in response to tooth contact indicating signals from the sensors. Such processing may include a calibration mode. During such a mode compensations can be made in tooth contacting signals arising from tightness of the teeth and other factors. More specifically, a standardized mechanical impact may be applied respectively to each tooth. The sensor output for that tooth, and from other sensors arising from the indirect transmission of vibrations arising from the application of the calibration impact, may be measured. The software can use this information to filter or separate out secondary signals produced by a sensor arising from the contact of adjacent teeth from the primary signals produced by a sensor when the tooth it is monitoring is directly contacted. Again, the present invention is not limited to a particular type of signal processing circuit in its broader aspects.

As yet another aspect of the present invention, a conventional jaw tracking device may be coupled to a computer for use in determining tooth contact variations correlated to various jaw closing trajectories in the sagittal and frontal planes. Utilizing this approach, a mapping of tooth contact results may be obtained for various jaw trajectories to provide a complete map of the occlusal interface. This information is utilizable by a dentist or other professional in devising a treatment plan for a patient.

In addition, the present invention relates to methods of determining tooth contact, as well as the sequence of tooth contact, and other information concerning tooth contact in response to shock pulse displacement or vibration signals generated upon tooth contact.

Accordingly, it is one object of the present invention to provide an improved tooth contact sensing apparatus and method.

These and other objects, features and advantages of the present invention will become more apparent with reference to the following description and drawings.

BRIEF DESCRIPTION OF THE DRAWINGS

FIG. 1 is a plan view of a patient's jaw and teeth which illustrates sensors directly coupled to the nonbiting surfaces of the teeth.

FIG. 2 is a side elevation view of a portion of the upper and lower jaws of a patient illustrating plural sensors directly coupled to the outer surfaces of the upper teeth.

FIG. 3 is a block diagram of one embodiment of a tooth contact sensing circuit in accordance with the present invention.

FIG. 10B is a vertical sectional view taken through a portion of the bite fork of FIG. 10A to illustrate a sensor as it is slid along the bite fork into position.

FIG. 10C is a vertical sectional view of the bite fork taken in the same manner as FIG. 10B, except with the sensor shown in position against a patient's tooth for sensing tooth contact.

FIG. 11 illustrates the distal end portion of the bite fork of FIG. 10A to show in greater detail a retentive element utilized in engaging the back teeth of a patient to rigidly and temporarily support the bite fork in position at such location.

FIG. 17 is a block diagram of one form of digital circuit used in processing signals in the embodiment of FIG. 15.

DETAILED DESCRIPTION OF PREFERRED EMBODIMENTS

Figure 4:
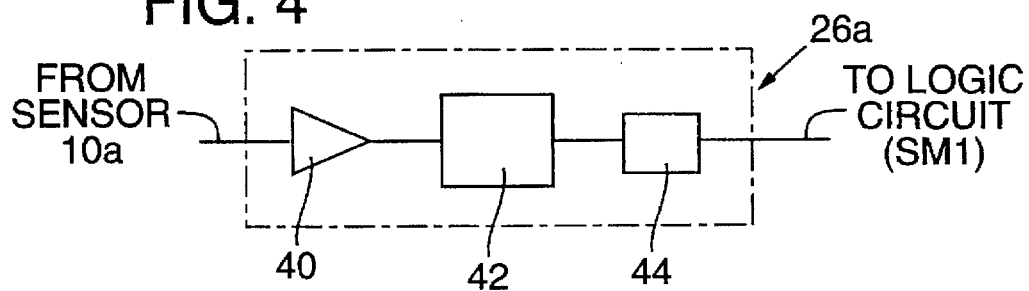
FIG. 4 is a block diagram of one form of a single channel of a signal shaping or conditioning circuit utilized in the sensing circuit embodiment of FIG. 3.

With reference to FIGS. 1 and 2, the present invention includes at least one tooth contact sensor, and most preferably a plurality of tooth contact sensors, coupled to the non-biting surfaces of teeth for detecting contact between the tooth to which a respective sensor is coupled and another tooth. FIG. 1 illustrates a plurality of sensors, in this case eight sensors, 10a through 10h, each coupled directly to a non-biting surface of an associated tooth; 12a through 12h. As explained more fully below, various mechanisms may be utilized for coupling the sensors to the teeth, with one approach illustrated in FIG. 1 comprising directly mounting the sensor to outer side surfaces of the teeth. A suitable adhesive may be utilized for temporarily mounting the sensors in place, such as an adhesive of the type used in temporarily mounting other dental appliances to teeth. The sensors 10a through 10h each produce a respective output signal indicating the tooth to which the sensor is coupled has made contact with another tooth. The signals from the sensors are carried by respective wires or cables, collectively referred to as 14 in FIG. 1, to a signal processor. Although the sensors may be mounted to both upper and lower teeth, in FIG. 1 the sensors are shown coupled to teeth 12a through 12h of an upper jaw 16 of a patient whose bite is being evaluated and/or treated by a dentist or other health care professional.

FIG. 2 illustrates the placement of these sensors on side surfaces of the teeth 12e through 12h.

By eliminating the need to place marking paper or other devices between the teeth in order to detect premature tooth contact, distortions caused by these between-teeth inserted devices are eliminated.

The output signals from the respective sensors (which includes representation of such signals or signals derived therefrom) may be processed to determine, for example, which tooth is contacting first. With this information, a dentist or other individual may treat the first tooth which contacts, for example by drilling, shaving or grinding the contacting portion of this tooth gradually until tapping of the jaws together confirms that this tooth is no longer prematurely contacting. Then, in further jaw closings, the next prematurely contacting tooth may be identified and treated. This process may be continued until all of the teeth, during jaw closing, contact substantially simultaneously or within a desired time interval.

To aid in this treatment process, the signals may be processed to provide other information, as explained more fully below. For example, the signals from the various sensors may be simultaneously monitored to determine the sequence at which the teeth contact one another. Consequently, early on, the dentist or other treatment professional is aware of which teeth may need treatment. Also, to provide a reliable indication of the extent of the problems a patient is having with bite stability, the time between first and subsequent tooth contact, and in particular between first and last tooth contact, may be determined. The longer this period of time, the greater the bite instability of the particular patient. Also, utilizing an optional jaw trajectory determining device, variations in tooth contact which occur depending upon jaw trajectory may be mapped to more fully evaluate the patient's bite stability to aid the treatment professional in designing an appropriate treatment regimen for the patient.

The sensors may take various forms, but most preferably comprise shock pulse or vibration sensors which respond to the shock pulse generated as the teeth contact one another. When teeth make contact, they move in their sockets and initially accelerate. This vibration and/or acceleration may be detected to indicate when a particular tooth has made contact with another tooth or teeth. Thus, a preferred form of sensor is a vibration sensor or an accelerometer. More specifically, a piezoelectric vibration sensor or accelerometer is a specifically preferred example. One suitable sensor is a piezoelectric vibration sensor Model 352 B-22 from PCB Piezotronics, Inc. of DePew, New York. Another form of most preferred sensor is a piezoelectronic shock pulse sensor such as a model 601210 shock pulse sensor from Apollo Research, DePew, New York.

Typically, the sensors are packaged in a water-impermeable, sterilizable housing, such as of stainless steel, and are of relatively small size. For example, suitable sensors may be one-quarter inch by one-quarter inch by one-quarter inch or smaller, and may be provided in housings with curved edges so as to not irritate the patient's mouth during use. Again, as explained more fully below, the sensors may be affixed or coupled to the teeth in any convenient manner. By affixing them to the outer side surfaces of the upper teeth utilizing an adhesive or wax resin, the sensors do not change the bite. It is important that the sensors be of a type which does not interfere with the patient's bite, as the purpose of the sensors is to sense or detect information concerning the natural contact of the teeth, and more particularly concerning the order in which the teeth contact one another.

Other impact detecting devices affixed to individual teeth may also be used. Small microphones are a possibility, however they suffer from the drawback of interference from signals from adjacent teeth which can distort the results.

Because the teeth move vertically relative to one another during chewing or biting, as explained above, vibration sensing is particularly suitable as there is little transfer of interfering signals from adjacent teeth, although typically some filtering of sensor output signals may be employed.

The information from the sensors enables dentists or others to reliably determine if one tooth is higher than others, and thus is traumatizing the tooth or forcing the muscles that close the jaw to close the jaw in an accommodative trajectory to avoid traumatizing the tooth, and devising a treatment plan to address such problems.

The first tooth to contact is of primary clinical significance, with other information being secondary, although useful. For example, the time between the first and last tooth contacts provides an indication of how stable the bite is, with a two microsecond delay time, for example, indicating a generally stable bite and bite equilibrium. A longer interval between first and last contacts implies that the professional should consider more work in stabilizing the bite (increasing the simultaneity of tooth contacts) to bring the interval down to an acceptable level, whether that be two microseconds or some other delay time. Also, the time between successive tooth contacts gives more information about bite stability. For example, a long interval between one tooth contact and the next tooth contact indicates that a jaw is sliding on the first tooth contact. In addition, because a bite does vary depending upon jaw trajectory, it is preferable to have a patient tap the teeth together multiple times, for example thirty or forty times, or more, to evaluate which tooth hits first all or most of the time, and thus identify the tooth or teeth requiring initial treatment.

Figure 13:
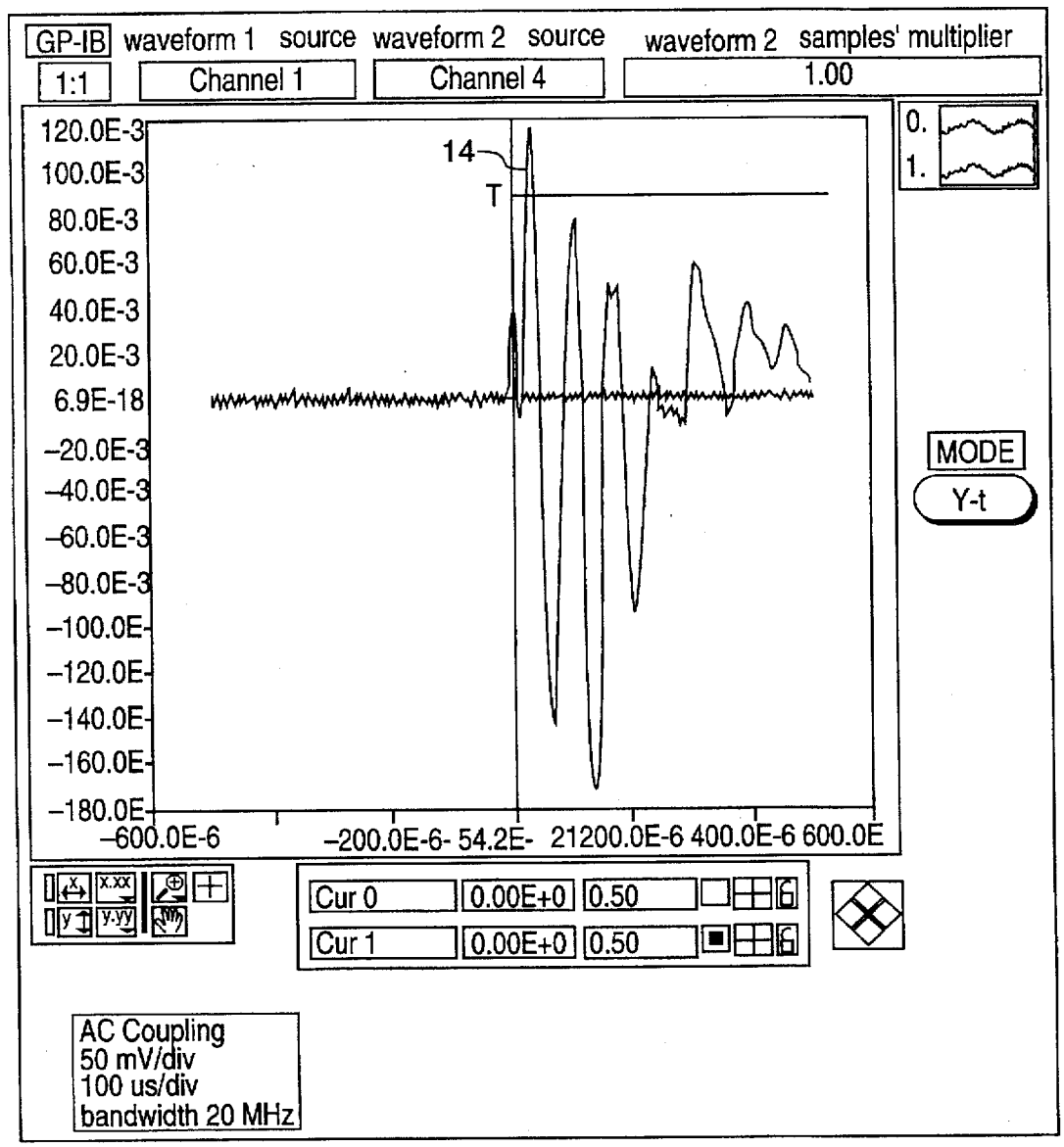
FIG. 13 is an illustration of a signal produced by a sensor upon contact by the tooth to which the sensor is coupled with another tooth.

Signals from the sensors 10a through 10h, or such other number of sensors as may be used, are processed to determine tooth contact information. The sensors may simply be coupled to an oscilloscope or other direct monitoring device in one form of signal processing. With reference to FIG. 13, a typical signal from a sensor generated upon tooth contact is displayed. In this case, the amplitude of the signal is along the Y axis and the time is along the X axis. The horizontal line identified by the letter T in FIG. 13 represents a threshold level, which may be varied. Detection of a signal having an amplitude in excess of the threshold, such as the portion of the signal indicated by the number 14 in FIG. 13, corresponds to contact by the tooth to which the sensor is coupled. Signals from tooth contact sensors may be delivered to various channels of an oscilloscope or to different oscilloscopes, with the dentist then monitoring the channel and time of tooth contact indicated in the displayed signals for determining information concerning tooth contact. The signal processing circuit may, of course, take other forms.

FIGS. 3, 4, 5 and 6A and 6B illustrate another form of signal processing circuit.

With reference to FIG. 3, the signal processing circuit comprises a sequence or signal detection circuit 20. The illustrated circuit 20 has a plurality of signal processing channels 24a–24h for evaluating signals delivered thereto by respective sensors, in this case sensors 10a through 10h. In this specific form of signal processor 20, one channel is associated with each of the detectors respectively. More or fewer channels would be used depending on the number of sensors employed in this particular embodiment. Each channel includes a signal shaping or conditioning circuit, indicated as 26a through 26h in FIG. 3, and associated logic circuits 28a through 28h. The outputs of the respective channels from the logic, circuit 22 are delivered to a display and/or indicator apparatus 30. The apparatus 30 may comprise a data storage mechanism, such as a computer, which may simply store all of the data that is collected for subsequent processing. Alternatively, a monitor or other display, such as a panel of light emitting diodes, may be utilized to indicate tooth contact and other information. Furthermore, the device 30 may comprise a printer for printing out the data delivered thereto by the respective signal channels. Furthermore, the device 30 may comprise a combination of these or other types of display devices.

In FIG. 4, one of the signal shaping circuits 26a is shown. This specific form of signal shaping and conditioning circuit includes an amplifier 40, a frequency shaping circuit such as a band pass or a low pass filter 42 and a digital signal forming circuit or device 44. The amplifier, which may be a variable gain amplifier, provides a signal of a magnitude which is sufficient for triggering the digital signal forming circuit. Circuit 44 provides an output at the appropriate logic level for the digital logic circuit or sequence detector 28a. Although the vibration sensor may produce a signal of sufficient amplitude, the inclusion of an amplifier 40 enables very weak signals from the sensors to also be detected. Since individuals tap their teeth with varying levels of intensity, the provision of gain adjustment and an amplifier enhances the variety of conditions under which the embodiment may be used.

The filter 42 is designed to filter out high frequency noise, and direct current and low frequency signal components, such as noise generated by electromagnetic interference. Although the filter is optional, it is preferred as an appropriate way of eliminating the undesired signals. The band pass of the filter may be varied, but a preferred band pass range is between one kilohertz and ten to fifteen kilohertz.

The filter 42 thus eliminates low frequencies (e.g. under approximately 1 kHz), and high frequencies (e.g. above 10 kHz–15 kHz). Very little, if any, useful information on tooth contact is believed to be carried by low-frequency and high-frequency signals. That is, most useful information is believed to be carried in the pass-band range of the filter 42 (i.e. 1 kHz to 10 kHz to 15 kHz. There is a difference in the spectral content of the direct signal and an "echo" (signal from an adjacent tooth). The direct signal will have more content at the higher end of the passband (i.e. toward 10 kHz or 15 kHz) in proportion to the lower end of the passband (i.e. closer to 1 kHz). An "echo", in contrast, will have less of those components near 10 kHz or 15 kHz in relation to the components near 1 kHz. In the time domain this is manifested by the direct signal having sharper peaks and steeper edges than the "echo" signal. This is believed due to the attenuation of higher frequencies of the "echo" signal by the soft tissue in which the teeth are set. This difference in spectral contents of the direct signal and an "echo" can be used to distinguish them. One practical method to distinguish between a direct signal and an "echo" is based upon a comparison of the rate of increase at these signals, i.e. the shape of their edges.

The filter 42 may, in addition, perform differentiation of the signals. Thus, derivatives may be compared against the threshold (two thresholds actually, a negative and a positive one, to make the circuit insensitive to the polarity of signals). The steeper signal (presumed to be the direct one), produces derivative of higher magnitude, and thus can be distinguished from an "echo".

The digital signal circuit 44 may comprise a simple conventional circuit, such as a Schmitt trigger which converts the signal from the other components of the signal shaping circuit 26a into digital signals having sharp transitions. The Schmitt trigger may be omitted in situations where the digital circuitry of the sequence detector or logic circuit 28a, in this case, is designed to function with relatively slowly-increasing signals. However, the circuit 44 does provide sharply transitioning signals and thereby facilitates detection of tooth contact by the associated logic circuit 28a.

Figure 5:
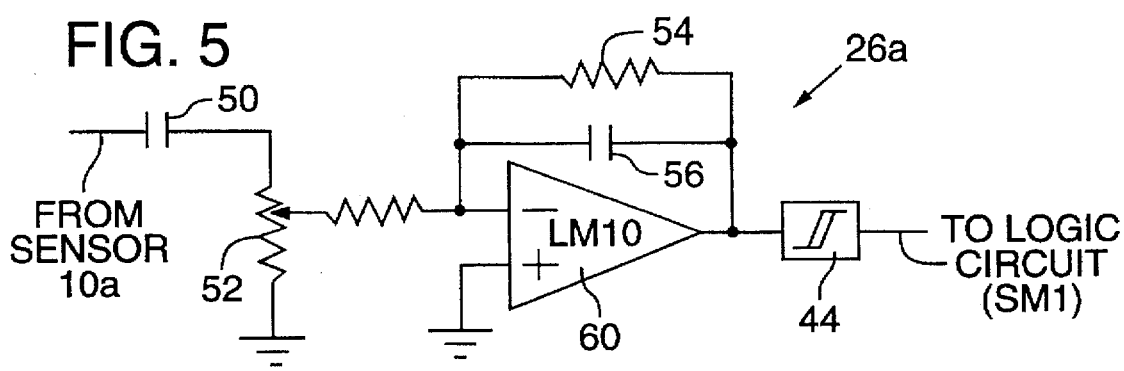
FIG. 5 is a schematic diagram showing the circuit of FIG. 4 in greater detail.

A specific implementation of the circuit of FIG. 4 is shown in FIG. 5. In this circuit, the capacitor 50 and resistor 52 form a high-pass filter having a corner frequency determined by the product of C1×R1, wherein C1 is the capacitance of capacitor 50 and R1 is the resistance of resistor 52. The resistor 52, in this case may comprise a potentiometer, and thus allows altering of the gain of the circuit to trigger upon desired signals (from sensors detecting the meeting of teeth) and to prevent triggering on signals transmitted as an acoustic wave from other teeth. Such secondary signals from other teeth are generally weaker and additionally have less steep edges and weaker high frequency components. The feedback network comprising the parallel resistor 54 and capacitor 56, between the inverting input of amplifier 60 and the output of the amplifier, provides the low pass filtering for the circuit. The corner frequency of the low pass filter is determined by the product C2×R3, wherein C2 is the capacitance of capacitor 56, and R3 is the resistance of resistor 54. Amplifier 60 comprises, in this case, an operational amplifier with a low power supply voltage and adequate frequency response, such as an LM10 amplifier from National Semiconductor Company. The Schmitt trigger 44 may be obtained from any of a variety of vendors. An exemplary Schmitt trigger is a 74 HC14. The circuit of FIG. 5 may be implemented in any conventional manner and may be a part of an application specific integrated circuit.

Figure 6A:
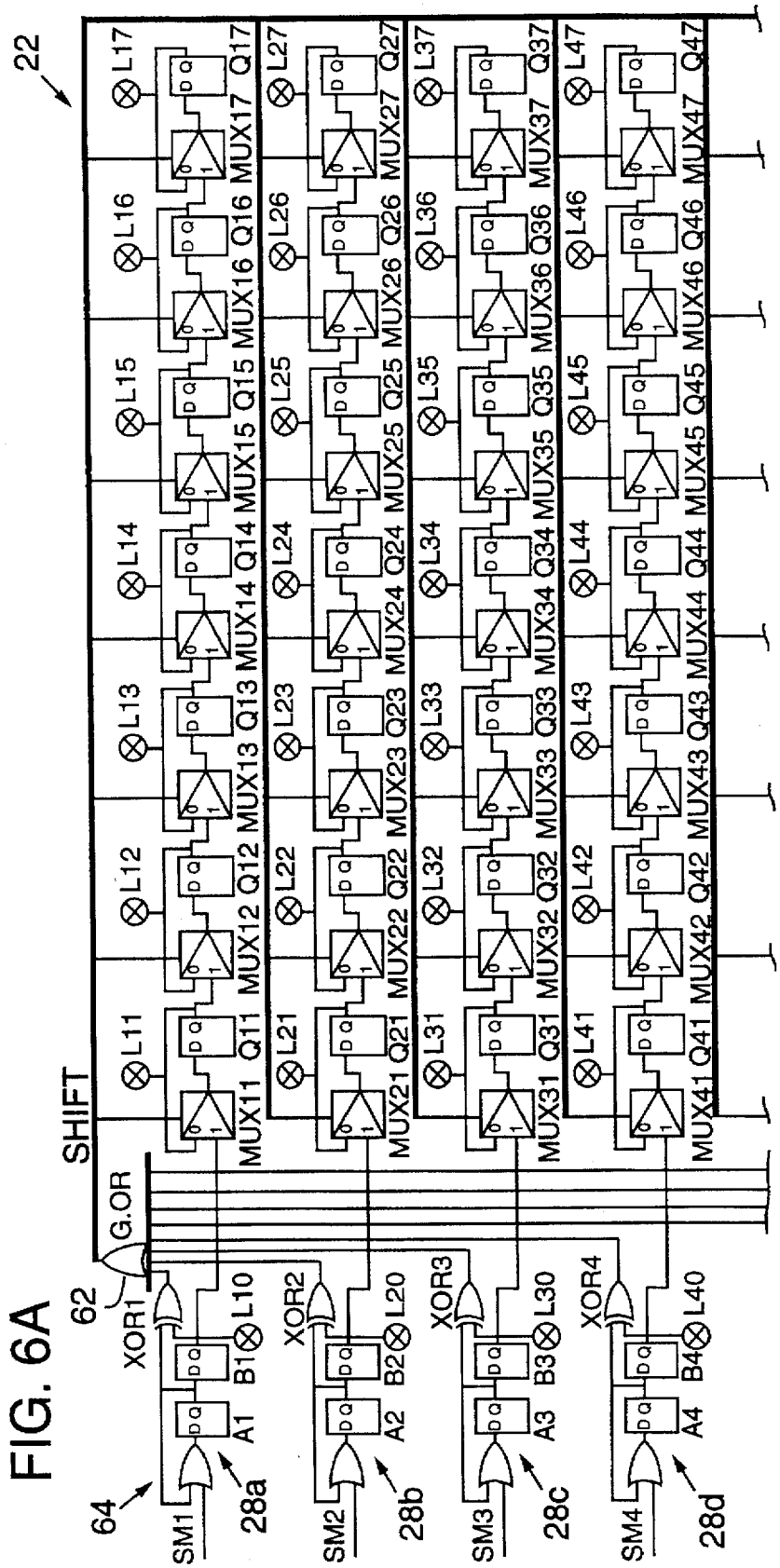
FIGS. 6A and 6B together are a schematic circuit diagram of one form of logic circuit utilizable in the embodiment of FIG. 3.
Figure 6B:
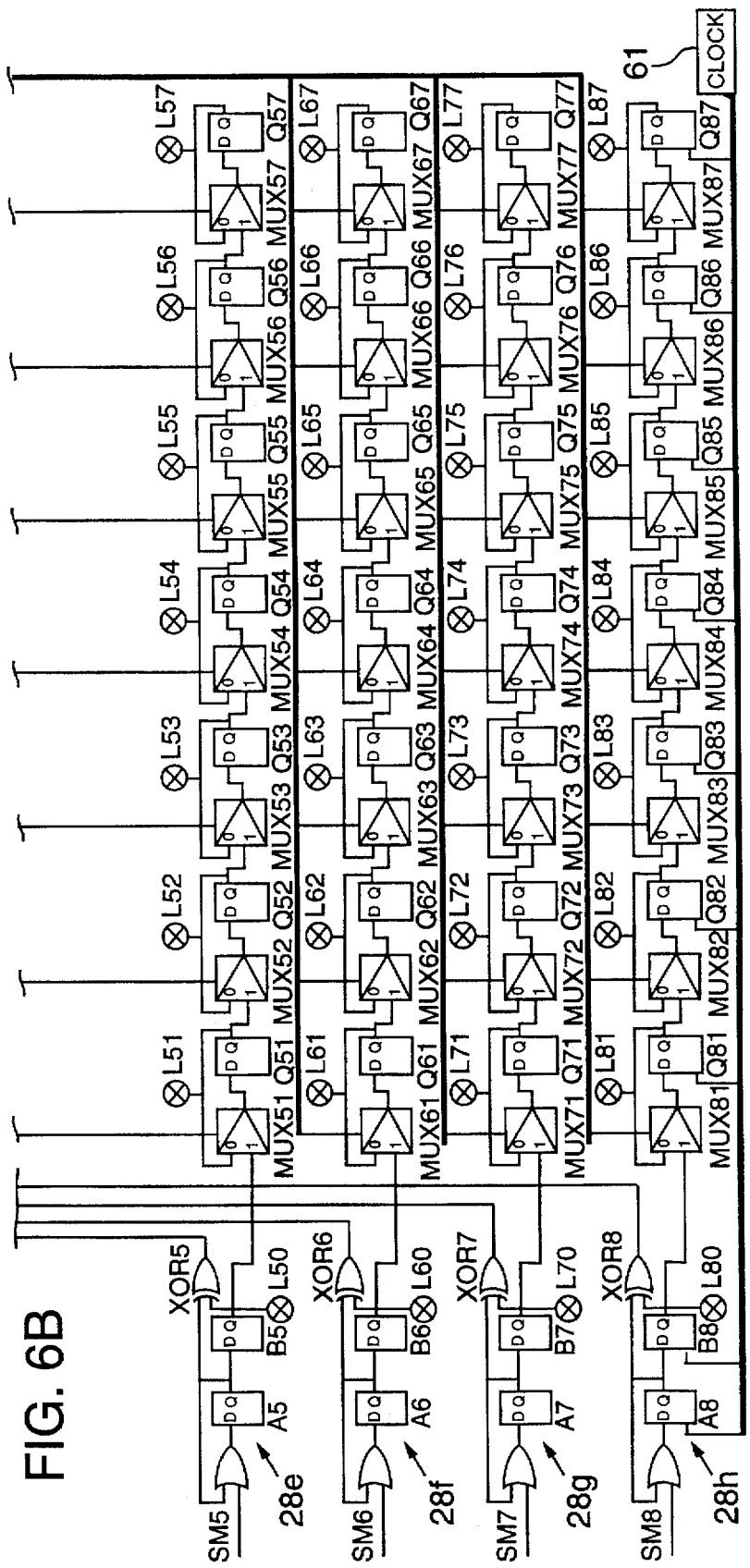

A detailed schematic diagram of a suitable logic or digital sequence detector 22 is shown in FIGS. 6A and 6B. This circuit may be expanded, as will be readily apparent, to accommodate more than eight sensors. In the FIGS. 6A and 6B embodiment, as will be explained below, one form of display device 30 (FIG. 3) is incorporated into this circuit. The circuit shown in FIGS. 6A and 6B is highly regular and can be realized with inexpensive shift registers. In the general case, N bit shift registers are used, and in this illustrated case the shift registers are eight bit registers for an eight channel input circuit.

In addition, in this particular circuit, a number of D-type flip-flops are used operated from the same high-frequency clock 61 (a clock with a twelve microsecond period is one specific example, although this may be varied), which makes the circuit easy to test and modify, as well as reliable. Although each of the flip-flops of the various channels of the circuit shown in FIGS. 6A and 6B are coupled to the same clock, this clock 61, for purposes of illustration and so as to not clutter the diagram in FIGS. 6A and 6B, is shown coupled to the flip-flops of the lower-most channel 28h of the circuit. It should again be understood that the clock 61 is coupled in the same manner to the flip-flops of the other logic circuits 28a through 28g of the illustrated logic circuit 22 (which comprises one specific form of the circuit 20 of FIG. 3). In addition, the CLEAR signal that asynchronously resets each of the flip-flops to zero, would be coupled to each of the flip-flops, but is not shown in FIGS. 6A and 6B, again for clarity. The CLEAR signal would be connected to the CLEAR input of each flip-flop.

The signal processing circuit shown in FIGS. 6A and 6B may be modified in a number of ways, for example, the eight input GLOBAL_OR gate 62 may be factorized to a few OR gates with a smaller fan-in (for instance, three OR gates with a fan-in of three each). In addition, the shift registers in each channel or row may be realized by off-the-shelf shift registers as well as the shift registers in the columns may be realized in the same manner. The LEDs L[ij] may be, for example, realized by eight-LED enclosures.

The circuit of FIGS. 6A and 6B has a signal formation circuit portion 64 and a signal storage and display circuit portion 66.

The following description provides a detailed discussion of the specific circuit shown in FIGS. 6A and 6B.

The signal formation circuit 64 has eight inputs, SM[1], . . . , SM[8], . . . from the respective signal shaping circuits 26a through 26h and thus responsive to the signals from the sensors 10a through 10h. A change in these signals from original zero to one is recorded in flip-flops A[1], . . . , A[8]. Since the input to flip-flop A[i], i=1, . . . , 8 is through an OR gate, OR[1], . . . , OR[8], the flip-flop needs just a short signal 1 to turn on. Because of the OR gate, it remains in state ON, even if the input goes OFF again. This protects the circuit from multiple signal changes in SM[i] and logical hazards in them.

The signal from flip-flops Ai is shifted at the active edge of the clock signal 61 to flip-flops B[i], i=1, . . . , 8. Exor gates XOR[1], . . . , XOR[8] compare the state of flip-flop A[i] with the state of the corresponding flip-flop B[i]. If these two signals are the same, which means no change in filtered input sequences, the outputs of all gates XOR[1], . . . , XOR[8] is 0. The value of the GLOBAL_OR gate 62, being an OR, is thus also zero. If any of signals "i" changes, respective XOR[i] becomes 1, and GLOBAL_OR (denoted as G.OR in the Figure) becomes 1. The output of G.OR is a signal SHIFT, which is given to the signal storage and display circuit.

The signal storage and display circuit 66 in this case is composed of eight eight-bit shift registers controlled by SHIFT. Each bit of a shift register is composed from a D-type flip-flop and a multiplexer MUX[i, j]. When SHIFT= 1, the contents of each flip-flop of registers (except the right-most one) is shifted to the flip-flop next and to the right of it. For instance: Q[1, 1] is shifted to Q[1, 2], Q[1, 2] to Q[1, 3], . . . , Q[2, 1] is shifted to Q[2, 2], Q[2, 2] to Q[2, 3], . . . . When SHIFT=0, the contents of all the registers remain the same (which means, the shift through the multiplexer MUX[i, j] is done from a flip-flop to itself). For instance: Q[1, 1] is shifted to Q[1, 1], Q[2, 2] to Q[2, 2], . . .

Each column of flip-flops corresponds to a new triggered state of sensors. The time axis is thus displayed horizontally: the subsequent flip-flops in the array, Q[i, j], j=1, . . . , 8 correspond thus to states of the same sensor "i" in eight different moments of time.

Observing the array of LEDs, L[i, j], which is displayed in corresponding array format, one can easily find the order of the first moments that each signal SM[i] changed to "1".

The operation of the illustrated circuit 22 is as follows:

The user presses key CLEAR that clears all flip-flops. The array

| Time--> | 8765 | 4321 |
|---|---|---|
| Sensor / | | |
| SM[1] | 0000 | 0000 |
| SM[2] | 0000 | 0000 |
| SM[3] | 0000 | 0000 |
| SM[4] | 0000 | 0000 |
| SM[5] | 0000 | 0000 |
| SM[6] | 0000 | 0000 |
| SM[7] | 0000 | 0000 |
| SM[8] | 0000 | 0000 | is displayed. When SM3=1 (even for short time), the next state of the array looks like:

|      |      |
|------|------|
| 0000 | 0000 |
| 0000 | 0000 |
| 1000 | 0000 |
| 0000 | 0000 |
| 0000 | 0000 |
| 0000 | 0000 |
| 0000 | 0000 |
| 0000 | 0000 |

When SM5=1 (even for short time), the next state of the array looks like:

|      |      |
|------|------|
| 0000 | 0000 |
| 0000 | 0000 |
| 1100 | 0000 |
| 0000 | 0000 |
| 1000 | 0000 |
| 0000 | 0000 |
| 0000 | 0000 |
| 0000 | 0000 |

When SM8=1, the next state of the array looks like:

|      |      |
|------|------|
| 0000 | 0000 |
| 0000 | 0000 |
| 1110 | 0000 |
| 0000 | 0000 |
| 1100 | 0000 |
| 0000 | 0000 |
| 0000 | 0000 |
| 1000 | 0000 | and so on.

The rows of the array correspond thus to sensors, the columns to their new states; new states are always appended at the left.

The column A[i] in the circuit 64 is optional and is used to remove multiple responses to a signal at a single sensor. Without this column, it can happen that a response to single signal SM[4] would be:

|      |      |
|------|------|
| 0000 | 0000 |
| 0000 | 0000 |
| 0000 | 0000 |
| 1010 | 1010 |
| 0000 | 0000 |
| 0000 | 0000 |
| 0000 | 0000 |
| 0000 | 0000 |

The column B[i] is used to remove repetitions. Without this column, it can happen that a response to two signals SM[4] and SM[7] would be:

|      |      |
|------|------|
| 0000 | 0000 |
| 0000 | 0000 |
| 0000 | 0000 |
| 1111 | 1111 |
| 0000 | 0000 |
| 0000 | 0000 |
| 1111 | 0000 |
| 0000 | 0000 | and there would be no place in the array to display changes of the next signals.

Figure 7:
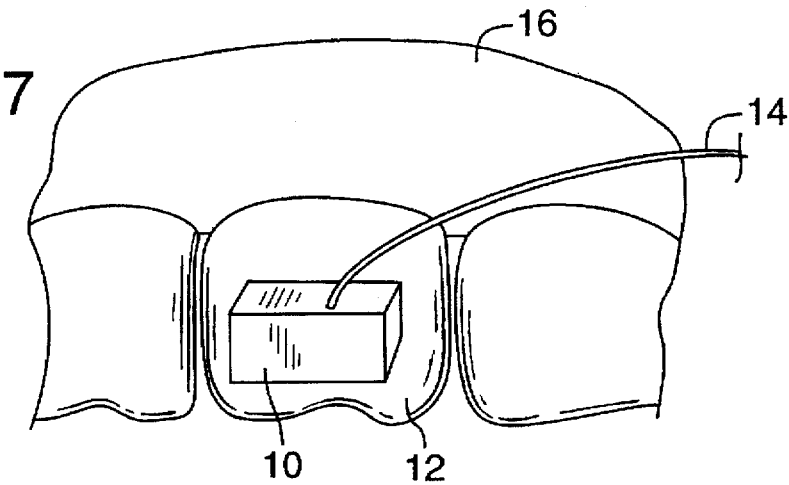
FIG. 7 is an enlarged view of a tooth with a sensor shown temporarily mounted rigidly to a non-biting surface thereof.
Figure 8:
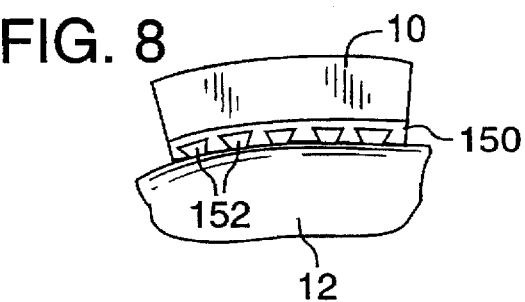
FIG. 8 is a bottom view of the sensor of FIG. 7 showing a sensor with a retentive plate used in securing the sensor to the tooth.
Figure 9:
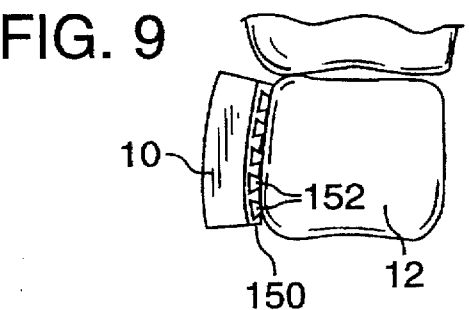
FIG. 9 is a side elevational view of the sensor of FIG. 8.

FIGS. 7–9 more specifically illustrate one method of mounting a sensor 10 to an associated tooth 12. The sensor 10 of these figures is shown with a retentive back 150 rigidly and permanently secured to the back of the housing of the sensor 10. The back 150 includes a plurality of longitudinal grooves, several being numbered 152 in FIGS. 8 and 9. Conventional dental adhesive is applied to the retentive back, with the back then being pressed against the tooth 12. The adhesive that fills the grooves, because of the undercut nature of the grooves, helps in more securely mounting the sensors to the teeth. Following use, the sensors are simply pried from the teeth in a conventional manner. The grooves 152 may then be cleaned of cured adhesive, the sensor sterilized and reused on the next patient.

In general, any device which holds the sensors temporarily against the non-biting surface of the tooth may be used. As another example, to illustrate the diversity of suitable devices, a bite fork sensor supporting apparatus is shown in FIGS. 10A through 10C and FIGS. 11 and 12. With specific reference to FIG. 10A, the illustrated bite fork comprises a horseshoe shaped sensor holding end portion, for positioning within a patient's mouth, a retentive mechanism such as a clasp for holding the back of the horseshoe shaped portion to the rearmost teeth of each side, and a flexible cable (not shown) on each side for carrying coaxial signal carrying conductors from the respective sensors out of the mouth and through the lips. More specifically, the illustrated bite fork includes first and second legs 300, 302 which are shaped to cross one another at respective locations 304 and 306. The legs 300, 302 are pivoted together at location 304 so that the bite fork may be opened and closed in a tong-like manner. Portions of the arms 300 and 302, indicated generally at 308 and 310, form handles which may be gripped by the user and operated to open and close the distal end 312 of the bite fork 290. A spring 314, or other biasing mechanism, may be used to bias the handle portions 308, 310 toward one another to in turn bias the distal end 312 of the bite fork to a closed position. The central portion of the bite fork 320 in this configuration comprises a staging area for a plurality of sensor assemblies 320a through 320j. The sensor assemblies slidably couple supported sensors (sensors 10a through 10e being shown in FIG. 10A) to the respective legs 300 and 302 in this staging area.

When the distal end of the bite fork is positioned or inserted into a patient's mouth, the number of sensors which are to be used for the particular patient are simply slid down the arms into position adjacent to the teeth to be evaluated. The sensors are moved into position against these teeth for sensing of premature tooth contact. The illustrated sensor assemblies and the functioning of these assemblies will be described in greater detail below. The portions of the respective arms 300 and 302 which are to be inserted into a patient's mouth may form a unitary portion of the respective arms 300, 302. The arms 300, 302 may be manufactured of a material such as stainless steel. However, in one preferred form of bite fork, the patient insert portions 330, 332 of the bite fork are made of a bendable material, such as copper tubing. Consequently, following insertion into a patient's mouth, these insert portions 330, 332 may be bent to position the supported sensors close to the teeth of the patient. Thus, the bite fork 290, and more specifically the sensor support portion thereof, may accommodate patients of varying mouth sizes and shapes. The insert portions 330, 332 may be coupled by a pin or dowel (the dowel 350 which couples insert portion 330 to the remainder of the leg 302 being shown in FIG. 10A). Retentive elements 352, 354 which may, for example, comprise a bendable wire, may be inserted into the ends of the insert elements 330, 332. When in a patient's mouth, retentive elements 352, 354 may be bent to engage the rear teeth (for example, the rear molars of the upper jaw) of a patient to provide support for the bite fork at the rear of the patient's mouth.

Following use on a particular patient, the insert portions 330, 332 may be discarded, the remainder of the bite fork may be sterilized, new insert portions 330, 332 and retentive elements 352, 354 may be placed in position, and the bite fork used with the next patient.

With reference to FIGS. 10B, 10C and FIG. 11, the individual sensor support assemblies and their operation will be described.

Support assembly 320g (FIG. 10B) includes an annular mount 360, in this case a cylindrical mount, having an interior opening 362 which is configured to match the outer circumferential shape of the corresponding insert element, in this case element 330. Although other shapes may be used, with insert elements of round circular cross section, opening 362 is correspondingly preferably round so that it may easily slide along the outer surface of the insert 330. A projecting arm or flange 364 is fastened at one end portion 362, as by spot welding, to the support 360. The flange 364 may comprise a relatively thin band of metal which is typically slightly wider than the width of the associated sensor 10g in this figure. The sensor 10g is coupled to the flange 364 by a biasing element such as a spring 368.

In operation, the sensor assembly 320g is slid along insert 330 into position adjacent to a tooth 12 to which the sensor 10g is to be coupled for sensing purposes. As shown in FIG. 10C, the sensor may then be pivoted into position against the tooth 12 with the spring 368 biasing the sensor against the non-biting surface of the tooth. A temporary retention element such as a set screw 370 may be tightened to prevent relative rotation between the support 360 and the insert 330 to retain the sensor in the desired position. Following use, the set screw is loosened and the sensor assembly, as well as the other sensor assemblies that are being used on the particular patient, are slid from the patient's mouth.

With reference to FIG. 11, the sensor assembly, which is at the rear-most position in the patient's mouth, may include a rigidifying sleeve 372 which surrounds the spring 368 of that sensor assembly. Consequently, when the retentive element 354 is positioned around the rear-most portion of the patient's rear tooth, the cylinder 370 bears against the non-biting surface of the tooth to assist in rigidifying the support of the bite fork at such location. Other retentive mechanisms may be used to temporarily support and mount the bite fork in the patient's mouth, such as rubber bands, adhesive, and/or thermoplastics or various impression materials commonly used in dentistry.

Figure 12:
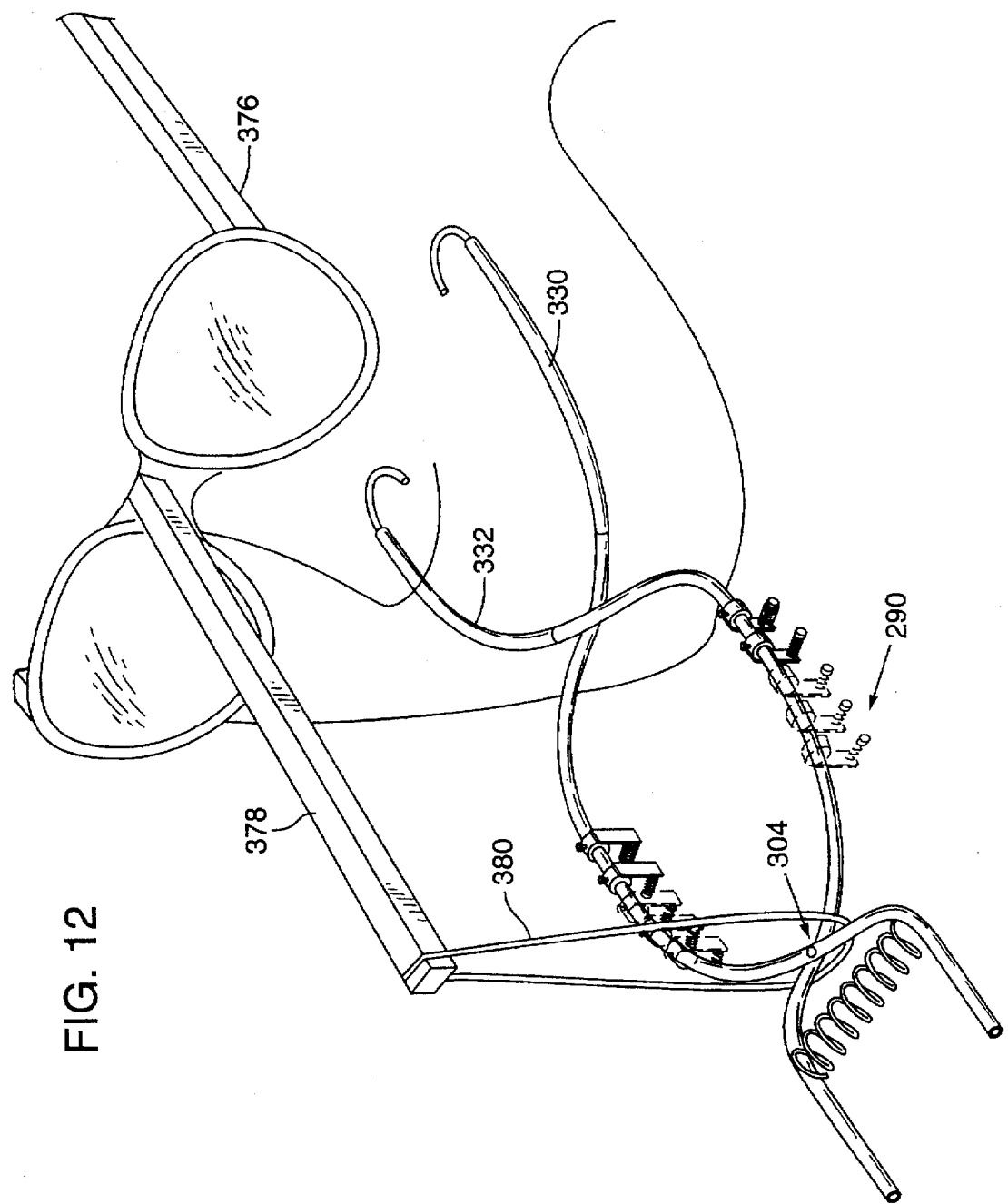
FIG. 12 is a perspective view of the bite fork of FIG. 10a shown supported within a user's mouth (although the user's mouth and teeth are omitted from this figure for convenience in illustration).

FIG. 12 illustrates a bite fork 290 with insert elements 330, 332 shown schematically inserted into a patient's mouth (the mouth not being shown for clarity). To provide support to the bite fork at the front of the patient's mouth, one suitable mechanism is shown. In this case, eye glasses 376 are used with a projecting rod 378. The rod 378 extends over a portion of the bite fork 290, in this case to the pivot location 304. A band, string, strap or other coupler 380 connects the bite fork to the projecting rod or element 378 to provide support for the bite fork at a location outside the user's mouth. In this manner, the bite fork is supported in a stable location both inside and outside of the patient's mouth.

Figure 10A:
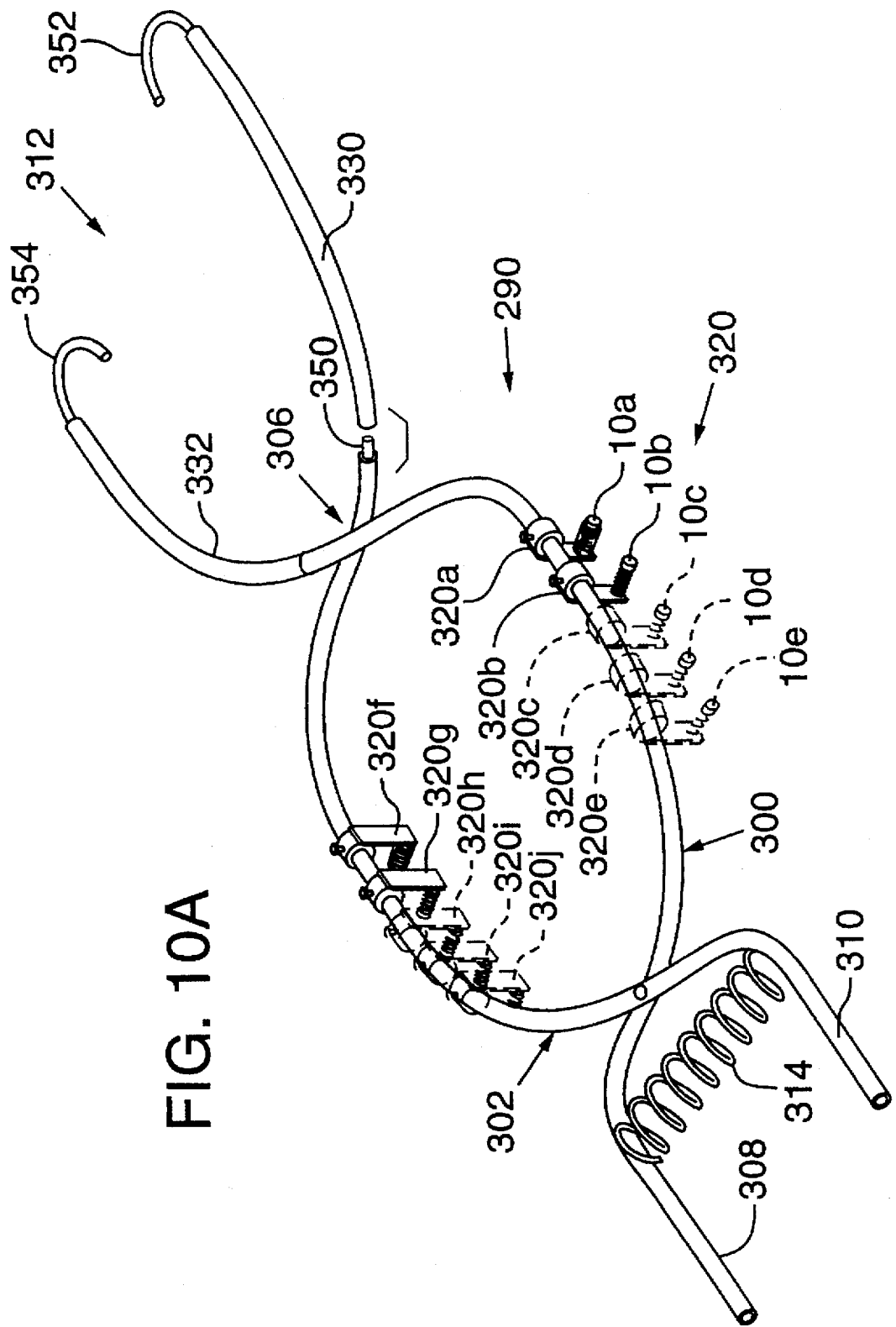
FIG. 10A is a perspective view of a bite fork in accordance with one embodiment of the present invention showing plural sensors slidably mounted thereto for movement into various positions against a patient's teeth.
Figure 10D:
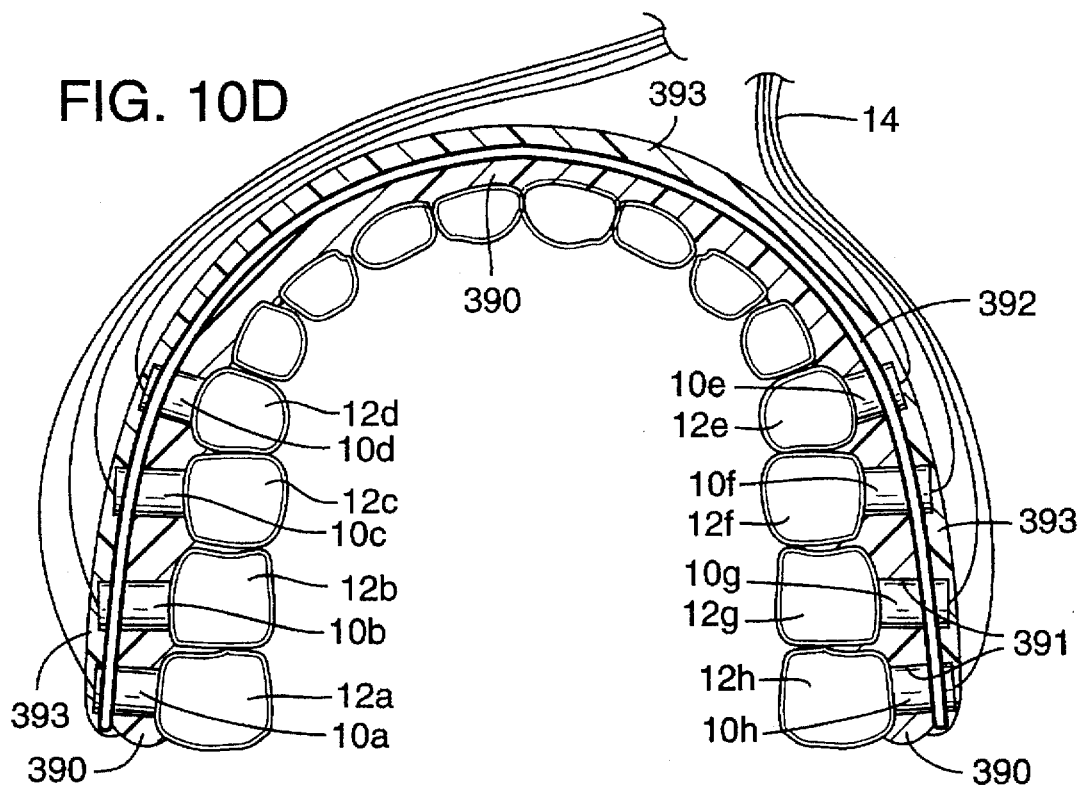
FIG. 10D is a perspective view of one form of a dental arch contour following support for positioning within a patient's mouth with sensors slidably coupled to the support.
Figure 10E:
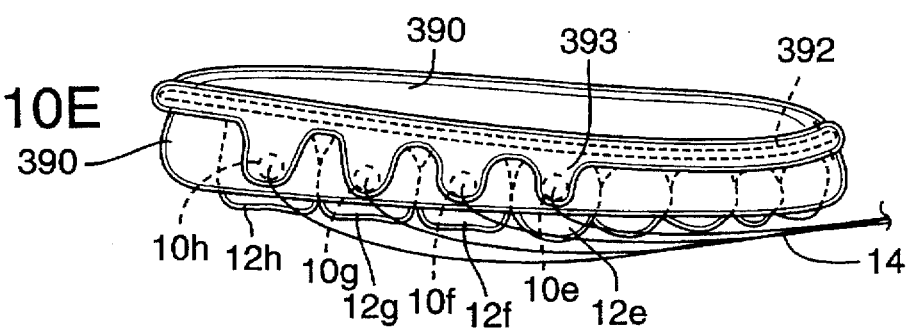
FIG. 10E is a side elevation view of the support of FIG. 10D.
Figure 10F:
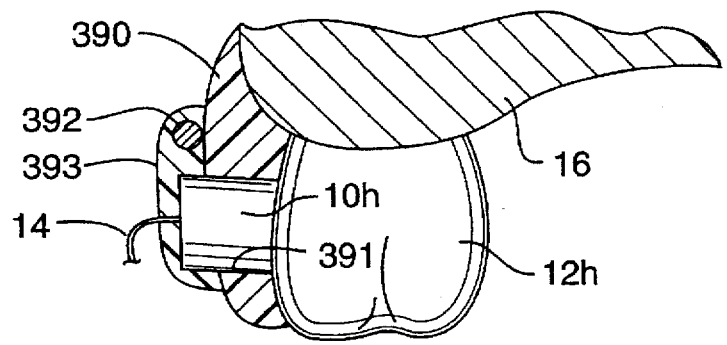
FIG. 10F is a vertical sectional view taken through a portion of the support of FIG. 10D.
Figure 10G:
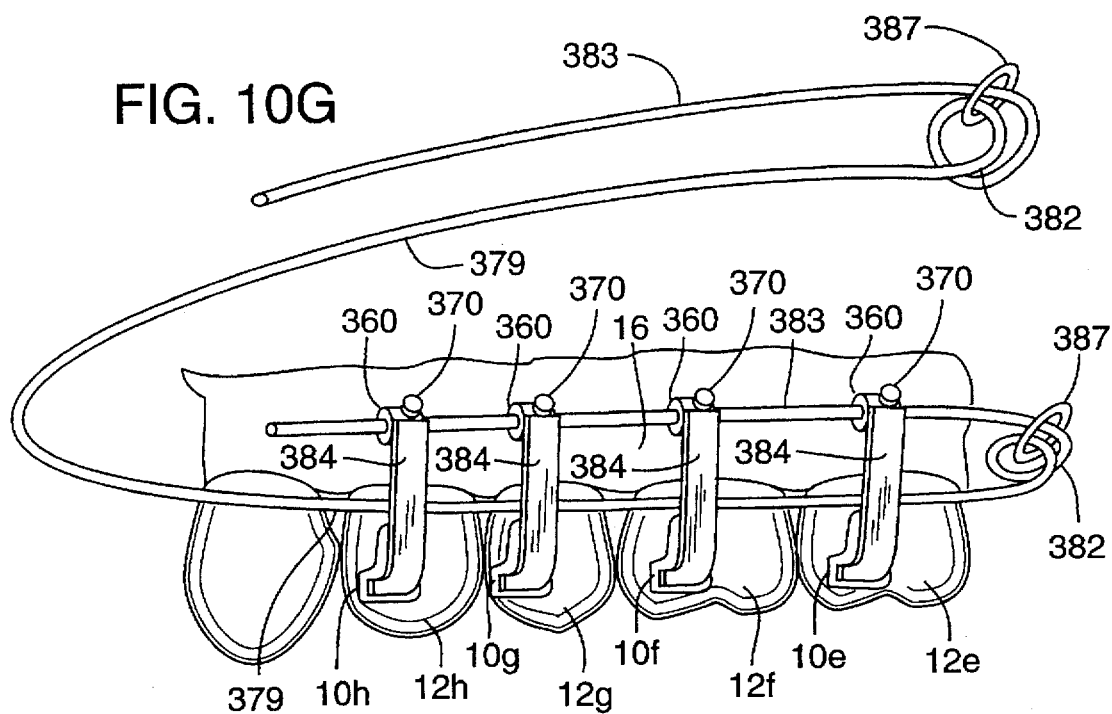
FIG. 10G shows an alternative form of dental arch contour following support.
Figure 10H:
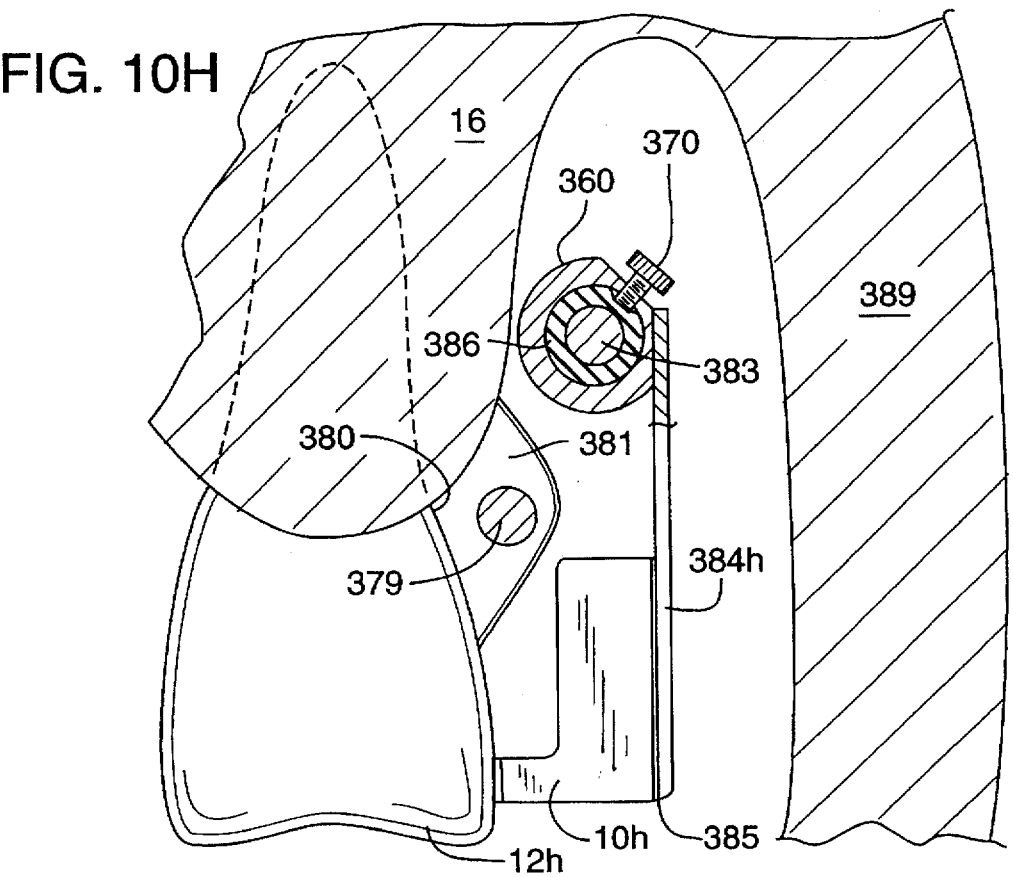
FIG. 10H is a vertical sectional view taken through a portion of the support of FIG. 10G.

An alternative sensor supporting apparatus for the coupling sensors to the upper teeth is illustrated in FIGS. 10G and 10H. In these figures, the conductors 14 have been eliminated for convenience. A resilient horseshoe or arch shaped sensor carrier, such as a spring steel wire 379, with 0.045 inch diameter piano wire being a specific example, is bent to apply an inwardly directed biasing pressure against the teeth when the carrier is inserted into a patient's mouth. The wire 379 rests in the groove 380 between the teeth 12 and the gum 16. This wire may be stabilized in position by, for example, molding a stabilizing material 381 around it (this stabilizing material option is not shown in FIG. 10G). The stabilizing material may be, for example, any of the various thermoplastics (such as TAK hydroplastic, TAK Systems, Wareham, Mass.) or putty impression materials (such as polyvinylsiloxane) commonly used in dentistry. The molding of material around the wire 379 may be accomplished in situ in the patient's mouth or remotely in a laboratory using a model of the patient's mouth. At each of the two rear (distal) ends of the spring steel wire, the illustrated wire is twisted into a helix loop 382. The ends of wire 379 terminate in sensor supporting arms 383 which extend forwardly toward the front of the patient's mouth along respective paths which are above the dental arch at each side of the patient's mouth. The sensors (10e-10h in this Figure as only sensors at one side of the mouth are shown) are each mounted on the sensor supporting arm 383 by a respective leaf 384. The leaves may be made of a resilient material, such as 0.010 inch thick stainless steel). The leaves 384 are each spot welded or otherwise attached to a respective support 360. The supports 360 are slidable along the arm 383 and can be fixed in a desired position, for example by tightening a set screw 370. The sensors are each preferably attached to their supporting leaf by a silicone glue 385 (or other flexible material such as a rubber cement). This dampens or minimizes the transfer of vibrations from one sensor up its support leaf to the frame or wire 383 and then back down another leaf and to another sensor. Dampening elements, such as rubber washers (or O rings), one being shown at 386 in FIG. 10H, may be positioned between each support 360 and arm 383 to further minimize the travel of vibrations from one sensor through the frame and to other sensors. The sensor support apparatus is thus positioned between a patient's cheeks 389 and the adjacent gum.

Arch wire spreading loops 387 may be coupled to the carriers at the loops 382. A tong-like pliers with arc-shaped gripping arms with tips that are insertable into the loops 387 may be used to insert the sensor support device into a patient's mouth. The handle portion of the pliers is manipulated with the gripping arms in loops 387 to spread the arch so that the apparatus is easily insertable into the patient's mouth. The pliers are then closed until the wire 379 shifts the sensors into engagement with the individual's teeth. The tongs are then removed from the patient's mouth.

A further alternative sensor supporting apparatus or carrier for the upper teeth is illustrated in FIGS. 10D, 10E and 10F. This illustrated apparatus is formed first by placing a non-rigid putty-like material 390 (such as a polyvinylsiloxane putty commonly used for dental impressions) against the teeth along the upper dental arch. This material sets and forms a horseshoe shaped arch which fits snugly against the outer (buccal) surfaces of the upper teeth. This step is typically either performed in situ in the patient's mouth or remotely on a model of the patient's mouth. This horseshoe shaped arch is then typically removed from the patient's mouth or model. Sensor receiving holes are drilled or otherwise formed in the arch at locations adjacent to each of the teeth which are to be evaluated for tooth contact during biting. Some of these holes are indicated at 391 in these figures. The arch with the holes is then typically placed on a plaster, gypsum or other model of the patient's mouth. At least one arch shaped reinforcing element, which may be of a resilient material, such as spring steel wire 392 (with 0.045 inch piano wire being a specific example) or of plastic, is affixed to the outside of the putty shaped arch in a position where it does not interfere with access to the holes 391. Putty adhesive or other material 393, which may be the same material as material 390, is used to hold the reinforcing element 392 in place. The reinforcing element imparts integrity and rigidity, and may, in the case of a wire or other inwardly biased element, impart an inward bias to the arch. Thereafter, the structure is typically removed from the model and the sensors are affixed in the holes 391, for example, by means of the same low viscosity polyvinylsiloxane material used to hold the reinforcing element in place. In this form, the sensor holding device is ready to be placed in the patient's mouth. The putty used to temporarily affix the sensors in place assists in dampening any cross vibrations between sensors.

Figure 14:
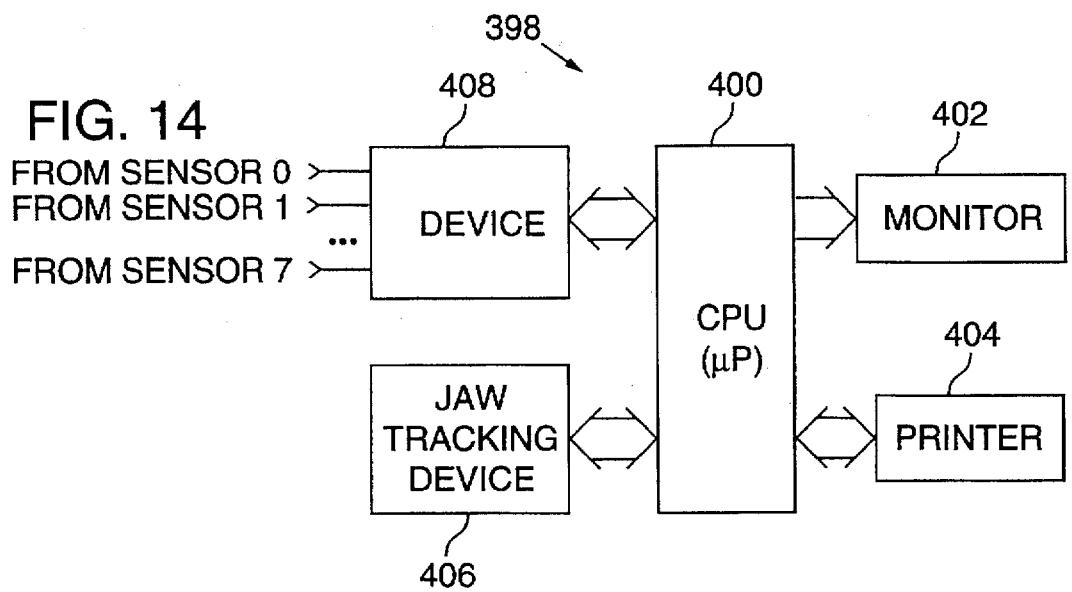
FIG. 14 is a block diagram of one form of a microprocessor or computer implemented apparatus in accordance with the present invention together with an optional jaw tracking device for monitoring jaw trajectory.

FIGS. 14 through 21 illustrate an alternative embodiment of the present invention utilizing a computer such as a personal computer or a microprocessor for processing the signals from the various sensors. With reference to FIG. 14, a block diagram of this form of the invention is shown. In this case, the description proceeds on the assumption that there are eight sensors, numbered 0-7. An appropriate interface couples the sensor output signals to the microprocessor 400 shown in this figure. The signals from the sensor may simply be processed to a form suitable for receipt by the microprocessor. However, sensor output signals may first be pre-processed, such as shown by the circuitry in FIGS. 6A and 6B or accumulated and then delivered to the microprocessor for further processing. It is expected that, as the microprocessor processing speed increases, direct signals from the sensors may be conditioned for inputting to the microprocessor for direct processing, such as by using an appropriate data acquisition circuitry, available commercially, and, in particular, data acquisition circuitry with A/D converters. The microprocessor may monitor the incoming signals to determine tooth contact information such as the first tooth contact, second tooth contact, and so forth. The microprocessor may determine other information such as the time between contact and time between first and last contact, as well as other information such as averaging tooth contacts to determine how many times a particular tooth on average is, for example, the first, second, or third first tooth to contact. The outputs from the microprocessor may be displayed on a conventional monitor 402 and may also be printed by a printer 404, each of which is coupled to the microprocessor. Ultimately, the microprocessor may simply collect data and store the collected data for subsequent analysis. The data may be stored in any convenient medium, such as floppy disks, CD Roms or hard disks. As will be apparent from the description below, the resulting data may be displayed in numerous ways, with some examples being specifically pointed out.

The illustrated system 398 may also have a jaw tracking device 406 coupled to the microprocessor. These jaw tracking devices monitor the jaw trajectory in the sagittal (front-to-back) and frontal (side-to-side) planes. For example, these devices may track jaw trajectories in 0.1 millimeter increments, as well as other increments, in the respective planes. One such jaw tracking device is the K-6 Kinesiograph, manufactured by Myotronics of Seattle, Wash.

The microprocessor can correlate information on the trajectory of the jaw with the corresponding data from the sensors for use in mapping the variations in tooth contact with jaw trajectory. By collecting enough tooth contacting data to cover the various jaw trajectories of interest to the healthcare professional, a complete map of the tooth contacting surfaces of the so-called occlusal interface is available. One can then drill down the contacting surfaces of selected teeth until the desired tooth contact results are achieved for substantially all of the various jaw trajectories of interest to thereby provide enhanced stability to the patient's bite.

A signal processing circuit 408 may be utilized to process the signals from the sensors to condition those signals for delivery to the microprocessor 400 along with other relevant information.

The signal conditioning circuit 408 typically has an autonomous power supply, an autonomous clock generator, and a display. Circuit 408 may also have the components shown in FIG. 3. The circuit 408 interfaces with microprocessor 400 by a standard computer interface. Such an interface allows for the transmission of the data from the device to the computer, under the direction of the computer.

Figure 15:
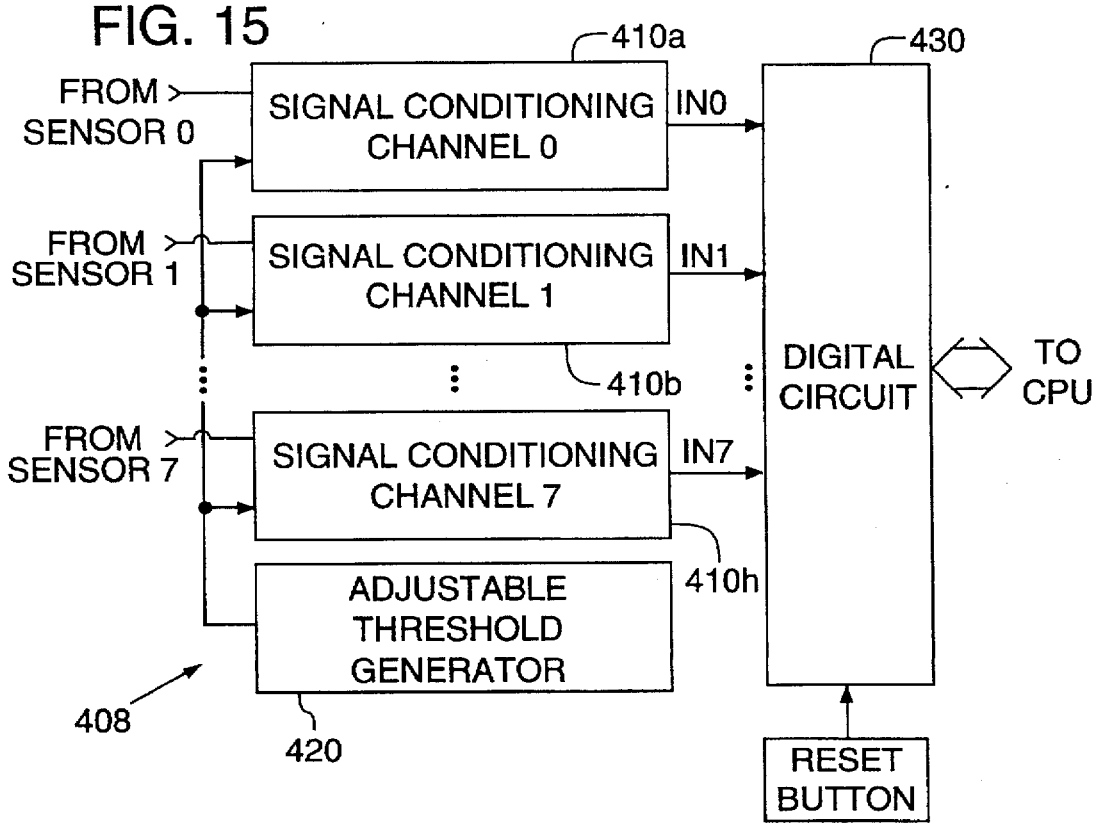
FIG. 15 is a block diagram of one form of a signal processing device or circuit for processing signals from the sensors into a form which is utilizable by the microprocessor.

The processing circuit 408 includes, in this embodiment, eight analog inputs from the respective sensors 0-7. The output of the circuit 408 is in digital form, typically having a channel associated with each of the sensors. With reference to FIG. 15, an expanded block diagram of the signal processing circuit 408 is depicted. The analog output of each sensor are each connected to a respective signal conditioning channel 410 (channels 410a through 410h are provided in the case of eight sensors, with signal conditioning channel 410a, 410b and 410h being shown in FIG. 15). As previously described in connection with the embodiment of FIG. 3, these signal conditioning and/or shaping circuits or channels amplify and filter the signal from the associated sensor. In the FIG. 15 form of the invention, an adjustable threshold generator 420 is provided to deliver a threshold signal to a respective input of each of the signal conditioning channels. Threshold generator 420 provides a threshold signal having a magnitude or value which is user adjustable. The amplified and filtered signals in the signal conditioning channels are compared against the threshold signal to produce a binary signal for delivery to a digital circuit 430 when the threshold is exceeded. These binary signal inputs are represented by the designations IN0, IN1 . . . IN7 in FIG. 15.

Figure 16:
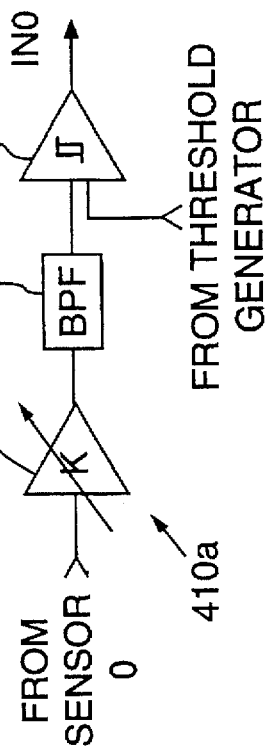
FIG. 16 is an illustration of a form of signal conditioning channel for the embodiment of FIG. 15.

FIG. 16 shows a block diagram for one of many possible implementations of the first (i.e. number 0) signal conditioning channel 410a (all other channels are identical). Each channel has an amplifier 432 having gain k, adjustable by the user. A band-pass filter (PBF) 434 (e.g. 1 KHz→10 KHz) may be included and can be realized as a part of passive feedback network of the amplifier 432, but it is shown as a separate block for clarity. The signal from the BPF is compared by comparator 436, preferably implemented with hysteresis, against a threshold from the threshold generator 420. As a result, a binary signal IN0 is produced and sent to the digital circuit 430. The design of BPF 434 is such that when there is no contact between the teeth where the sensor is connected, the signal from the sensors (either DC or very low frequency AC) falls into the stop band of the BPF. When a tooth contact occurs between the tooth associated with the sensor and another tooth (as a result of tapping, for example), the sensor 0 produces a damped AC signal having a substantial frequency component within the pass band of the BPF 434. Thus, several oscillations produced by the sensor are passed by the BPF and the signal on one input of the comparator crosses the threshold (see T in FIG. 13) connected to the other input of the comparator. The comparator has a passive feedback network around it to provide a small hysteresis. Hysteresis makes the comparator more immune to high-frequency (HF) noise which may be superimposed on the signal. The threshold is adjusted by the user in a way providing maximum immunity of the circuit to HF noise. The gain k of the amplifier is adjusted by the user to provide desired sensitivity to the signals from the sensors. When the gain k of the amplifier and the threshold voltage are adjusted properly, the circuit produces a LOW-HIGH binary transition on the IN0 line (or a sequence of such transitions) only upon a tooth contact. The transition(s) is (are detected by the digital circuit 430.

The present circuit may have a BPF with constant frequency parameters. However, the circuit may be provided with a BPF tunable by the user, if desired.

Figure 17:
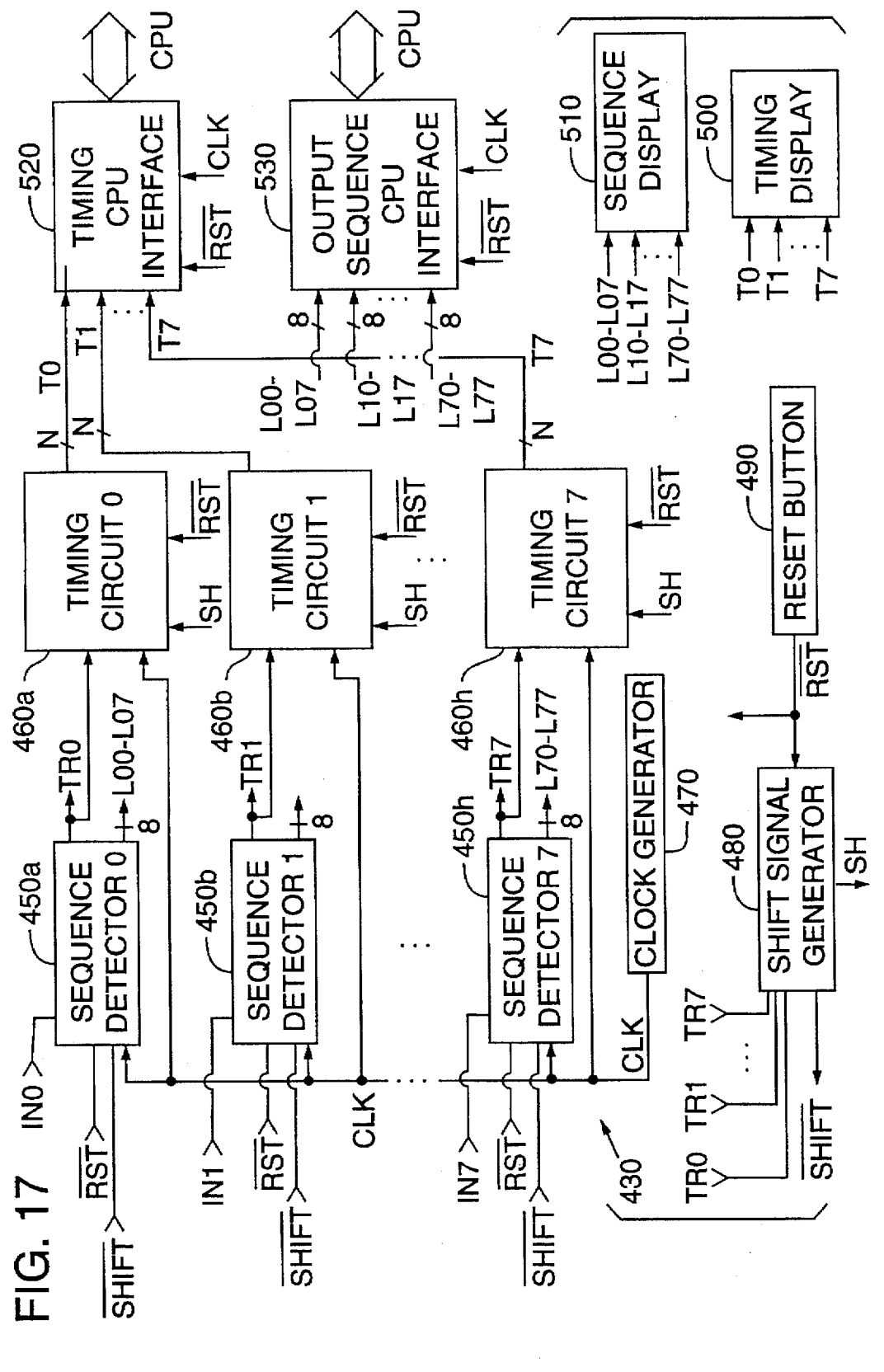

FIG. 17 shows a block diagram of one form of a digital circuit 430. It comprises eight sequence detectors 450a through 450h, eight timing circuits 460a–h, a clock generator 470, a shift signal generator 480, a reset button 490, two displays 500, 510 and two CPU interfaces 520, 530: for the timing data and for the sequence data. There are only nine input signals to this form of circuit: eight input signals IN0–IN7, and a reset button signal, $\overline{RST}$. For convenience, the components are not shown for all channels, although they are identical.

The other signals shown in FIG. 17 are internal signals.

Figure 18:
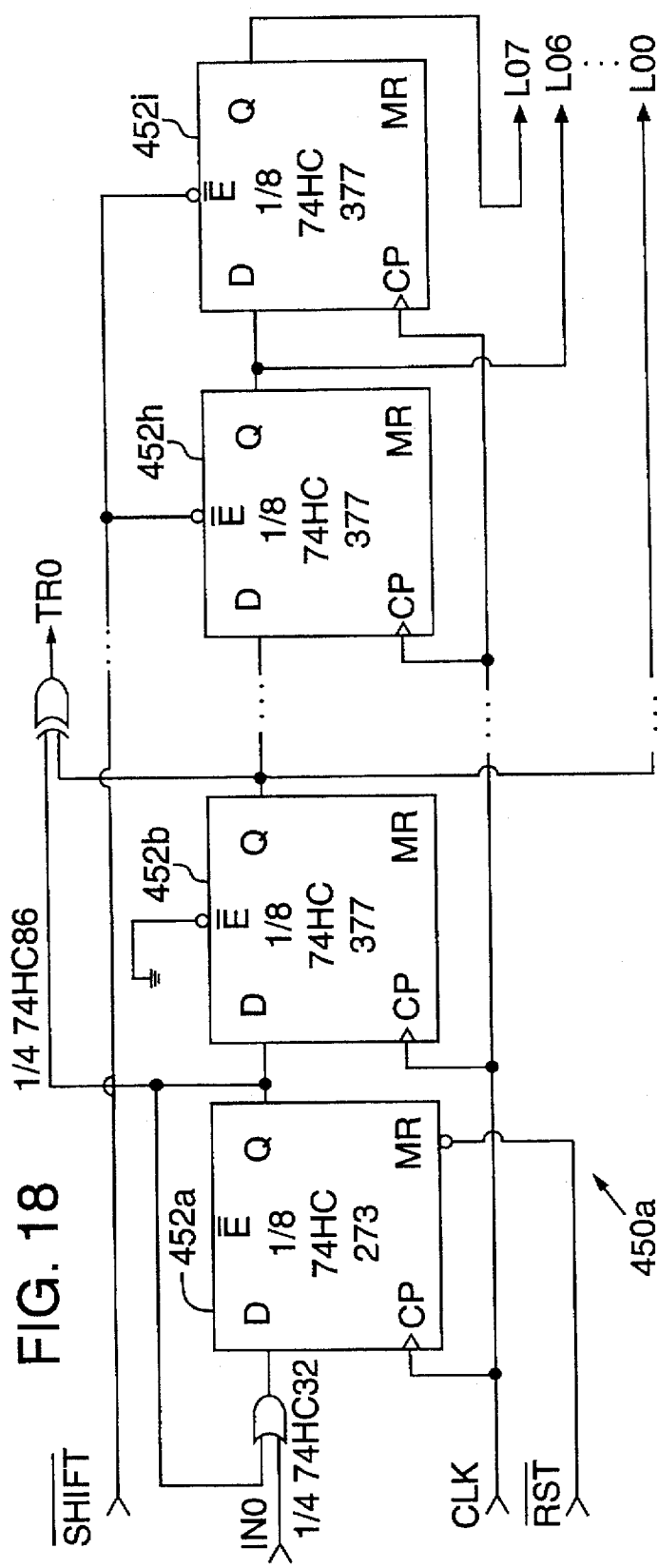
FIG. 18 is a schematic diagram of a single channel sequence detector.

FIG. 18 shows a schematic diagram of a single channel sequence detector 450a, the other sequence detectors being identical. Sequence detector 450a comprises nine D-type flip-flops 452a through 452i and some logic gates. The first two flip-flops 452a, 452b detect the first rising edge of the input signal IN0. The first flip-flop 452a is set into a logic state or state "1" by the first rising edge of IN0 and it remains in this state until it is reset asynchronously by the RST signal. The other flip-flops 452 serve as memory elements (shift register). Only one flip-flop 452b has the $\overline{E}$ (enable) input connected to LOW. The signals L00–L07 are connected to the sequence display 510 and to the output sequence CPU interface 530.

Figure 19:
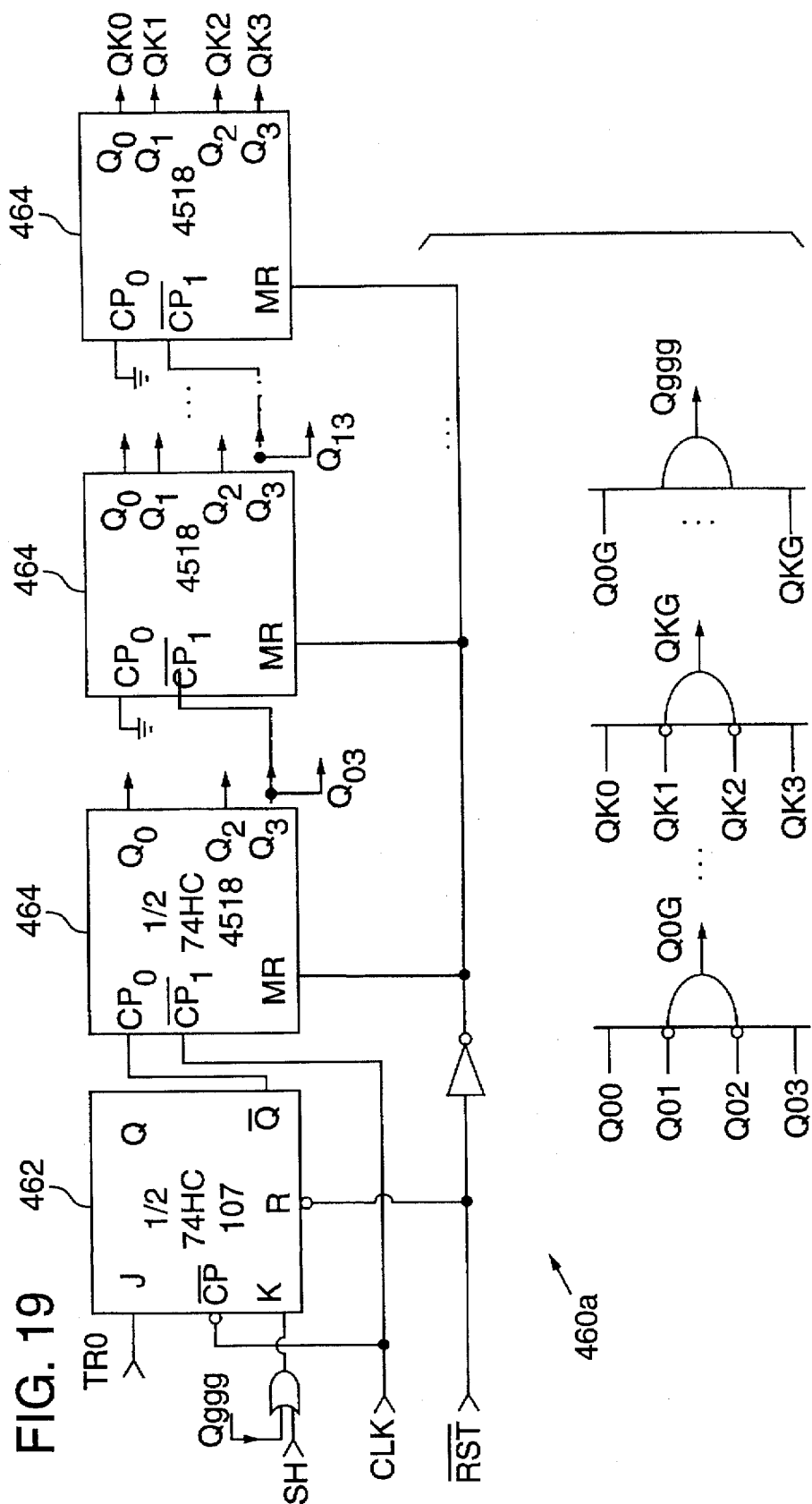
FIG. 19 is a schematic diagram of a single channel timing circuit.

FIG. 19 shows a schematic diagram of a single channel timing circuit 460a, the other such circuits 460b through 460h being identical. The JK-type flip-flop 462 produces a single pulse connected to the CP0 input of a first BCD counter 464. This is the least significant digit (LSD) of the number of clock pulses between the contact of the tooth in the given or associated channel and another contact (on any other tooth). In this arrangement, the cascade of counters 464 collects the number of clock pulses between the contact of a given tooth and any other tooth (multiple signals from a given tooth do not matter in this circuit). The Qggg signal is provided to reset the cascade of counters to 0 in case the given tooth contacted is the last one (there would be no other signal to stop counting). The 99 ... 9 state decoder can be easily modified to decode any other state than 99 ... 9 (such as 99 ... 8) in order to make the counter stop in another state other than 0. The exact number of the BCD counters in the cascade can be easily determined based upon the Clock CLK frequency and the longest desired time period to be recorded in any channel. The signals Q00–Q03, ... , Qk0–Qk7, representing timing data from a single timing circuit, are collectively denoted as T0. Likewise, T1, ... , T7, represent timing data from the other channels.

Figure 20:
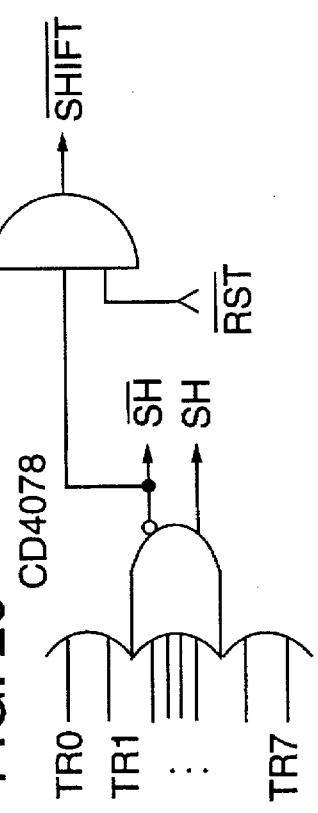
FIG. 20 is a schematic diagram of a shift signal generator.

FIG. 20 shows a form of shift signal generator 480 (FIG. 17).

Figure 21:
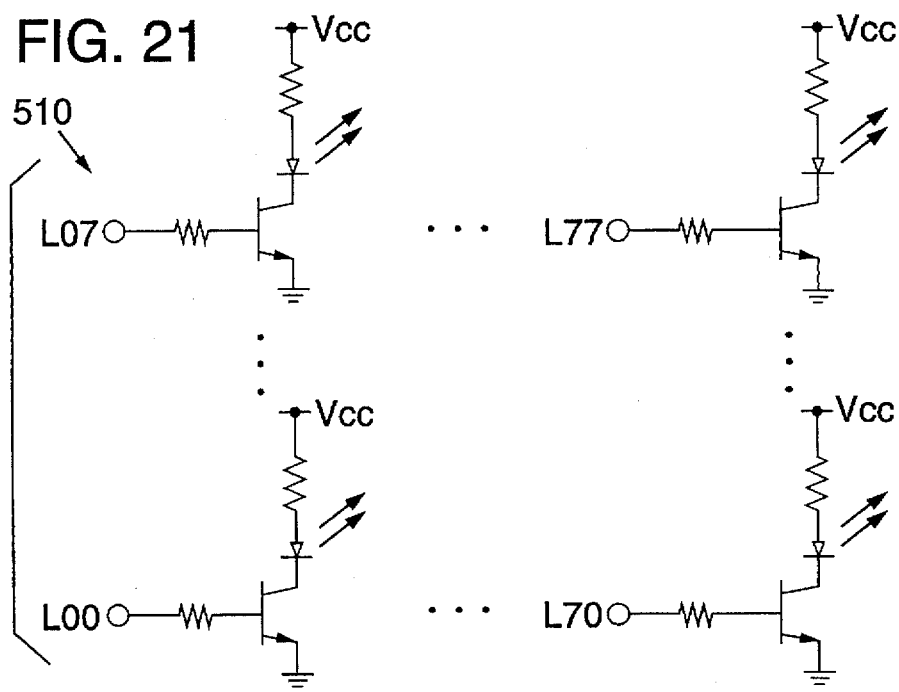
FIG. 21 illustrates one implementation of a sequence display.

FIG. 21 shows one implementation of a suitable sequence display 510 (FIG. 17) having plural LEDs.

Figure 22:
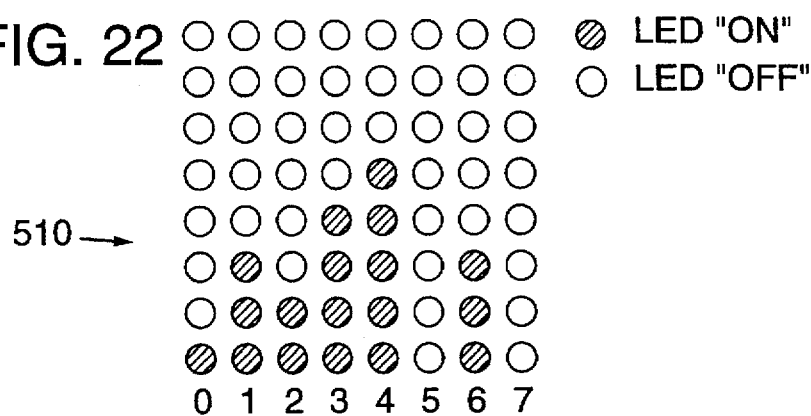
FIG. 22 illustrates an example pattern on the sequence display of the form of FIG. 21.

FIG. 22 shows an example pattern of LEDs (showing energized LEDs as dark spots) of the sequence display 510. It has the following interpretation: sensor #4 detected a tooth contact first. After certain number of clock cycles (not shown on the sequence display of this circuit), the sensor #3 detected a tooth contact. Then the sensors #1 and #6 detected their teeth contacts "simultaneously", i.e. within the same clock cycle (this is relatively rare and becomes almost impossible as the clock frequency is increased). Then the sensors #2 and #0 were triggered. It is desirable to have all sensors detect their respective teeth contacts within different clock cycles so that complete information about the sequence of tooth contacts can be obtained. It can be accomplished by having the clock generator frequency sufficiently high. It has been determined in experiments that the clock frequency of the order of 100 kHz is sufficient in most cases. Higher frequency can be used, especially to provide better resolution for timing data (collected by the timing circuits). However, too high frequency of the clock would lead to an unnecessarily large number of BCD counter blocks.

Figure 23:
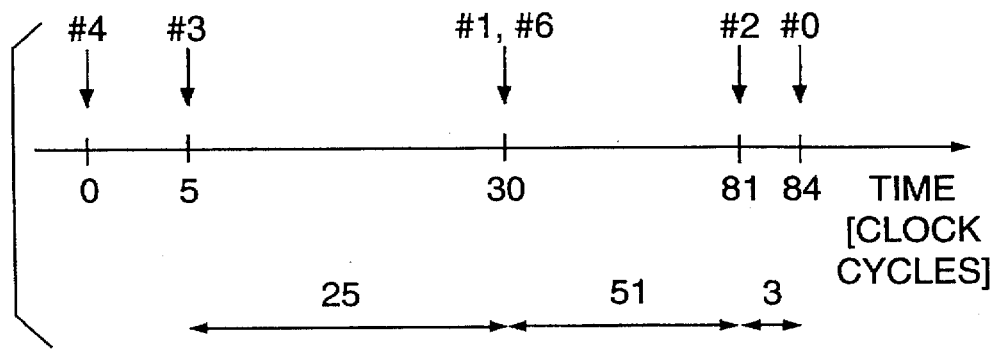
FIG. 23 illustrates one example of timing data for the sequence shown in FIG. 22.

FIG. 23 shows an example of timing data for the sequence in FIG. 22. Together with that sequence, one can read that: sensor #4 detected contact first. Five clock cycles later, sensor #3 detected a contact. Twenty-five cycles later, sensors #1 and #6 detected contacts in the same clock cycle. Fifty-one clock cycles later (T1=T6=51), sensor #2 detected a contact, and, finally, after another three cycles, sensor #0 detected a contact. Sensor #0 was the last one to contact, therefore its counter was reset to 0 after running into an overflow.

The implementation of the two CPU interfaces 520, 530 will vary depending on the particular computer interface used. Their implementation will be readily apparent to those of ordinary skill in the art.

The implementation of the timing display 500 is straight forward given that the timing data T0–T7 are represented in BCD form.

The clock generator 470 is preferably implemented as a crystal oscillator to provide a square waveform output of high frequency stability. If desired, a high-frequency oscillator with a programmable frequency divider can be used to allow programming of the clock frequency. Arithmetic circuits for the conversion of the number of clock cycles into time in milliseconds can be added. All these modifications will be readily apparent to those of ordinary skill in the art.

The host computer will read data from the device or circuit 408, and may optionally reset the device (in addition to a manual reset).

The following data structures may be read from the device via the computer interface (elements of C programming language notation will be used).

```
#define K 5 /* the number of BCD digits to represent timing
         data - 1 */
int L[8] [8];     /* ones and zeros representing
                   L00–L07, ..., L70–L77 */
int T[8] [K+1]; /* timing data in BCD format */
```

The above arrays correspond to the hardware format of the data in the device, therefore they can be easily read via the computer interface.

More data structures may be introduced to facilitate processing of the data in order to display it in the desired form.

```
int cumulative [8] [8];   /* cumulative [m] [n] represents
                           number of times tooth m was n-th
                           in the sequence - data collected
                           over several bite sequences */
```

-continued

| | |
|---|---|
| int time[8]; | /* timing data for one bite sequence - as a single number (as opposed to BCD representation in T */ |
| int tap[8]; | /* tap[m] == k means that the tooth m was k-th in the last bite sequence */ |

Example: the following sequences of bites were recorded:

Sequence A: #1, #5, #0, #4
Sequence B: #1, #0, #4, #3, #2
Sequence C: #4, #1, #2

The first sequence was recorded as the following L array by the device or circuit 408.

| | | | | | | | | |
|---|---|---|---|---|---|---|---|---|
| tooth #0 | 1 | 1 | 0 | 0 | 0 | 0 | 0 | 0 |
| tooth #1 | 1 | 1 | 1 | 1 | 0 | 0 | 0 | 0 |
| tooth #2 | 0 | 0 | 0 | 0 | 0 | 0 | 0 | 0 |
| tooth #3 | 0 | 0 | 0 | 0 | 0 | 0 | 0 | 0 |
| tooth #4 | 1 | 0 | 0 | 0 | 0 | 0 | 0 | 0 |
| tooth #5 | 1 | 1 | 1 | 0 | 0 | 0 | 0 | 0 |
| tooth #6 | 0 | 0 | 0 | 0 | 0 | 0 | 0 | 0 |
| tooth #7 | 0 | 0 | 0 | 0 | 0 | 0 | 0 | 0 |

This array is simply an image of the LED display printed "sideways" (a 0 corresponds to a D flip-flop in a "0" state and an LED "off", a 1 corresponds to a D flip-flop in a "1" state and an LED "on"). The other two sequences were represented likewise by the respective contents of the L array.

Each sequence would have the following tap array created:

| tooth # | 0 | 1 | 2 | 3 | 4 | 5 | 6 | 7 |
|---|---|---|---|---|---|---|---|---|
| Sequence A: | 3 | 1 | 0 | 0 | 4 | 2 | 0 | 0 |
| Sequence B: | 2 | 1 | 5 | 4 | 3 | 0 | 0 | 0 |
| Sequence C: | 0 | 2 | 3 | 0 | 1 | 0 | 0 | 0 |

A 0 in this array means that the corresponding tooth did not contact in this sequence.

Based on these data, the following cumulative array can be created for the three sequences:

| | 1 | 2 | 3 | 4 | 5 | 6 | 7 | 8 times |
|---|---|---|---|---|---|---|---|---|
| tooth #0: | 0 | 1 | 1 | 0 | 0 | 0 | 0 | 0 |
| tooth #1: | 2 | 1 | 0 | 0 | 0 | 0 | 0 | 0 |
| tooth #2: | 0 | 0 | 1 | 0 | 1 | 0 | 0 | 0 |
| tooth #3: | 0 | 0 | 0 | 1 | 0 | 0 | 0 | 0 |
| tooth #4: | 1 | 0 | 1 | 1 | 0 | 0 | 0 | 0 |
| tooth #5: | 0 | 1 | 0 | 0 | 0 | 0 | 0 | 0 |
| tooth #6: | 0 | 0 | 0 | 0 | 0 | 0 | 0 | 0 |
| tooth #7: | 0 | 0 | 0 | 0 | 0 | 0 | 0 | 0 |

The array tap for the example of FIG. 22 would be:

| tooth # | 0 | 1 | 2 | 3 | 4 | 5 | 6 | 7 |
|---|---|---|---|---|---|---|---|---|
| | 5 | 3 | 4 | 2 | 1 | 0 | 3 | 0 |

Adding this sequence to the data cumulated above would yield:

| | 1 | 2 | 3 | 4 | 5 | 6 | 7 | 8 times |
|---|---|---|---|---|---|---|---|---|
| tooth #0: | 0 | 1 | 1 | 0 | 1 | 0 | 0 | 0 |
| tooth #1: | 2 | 1 | 1 | 0 | 0 | 0 | 0 | 0 |
| tooth #2: | 0 | 0 | 1 | 1 | 1 | 0 | 0 | 0 |
| tooth #3: | 0 | 1 | 0 | 1 | 0 | 0 | 0 | 0 |
| tooth #4: | 2 | 0 | 1 | 1 | 0 | 0 | 0 | 0 |
| tooth #5: | 0 | 1 | 0 | 0 | 0 | 0 | 0 | 0 |
| tooth #6: | 0 | 0 | 1 | 0 | 0 | 0 | 0 | 0 |
| tooth #7: | 0 | 0 | 0 | 0 | 0 | 0 | 0 | 0 |

The following ANSI C program fragment converts data in L into data in tap:

```
int LL[ [8] = {0};
int i, j, n, h, tooth;
/* count number of 1's for each tooth and store in LL */
for (i = 0; i < 8; i++)
    for (j = 0; j < 8; j++)
        LL[i] += L[i] [j];
/* convert LL into tap */
n = 0;
for (h = 8; h > 0; h--) {
    for (tooth = 0; tooth < 8; tooth++) {
        if (LL[tooth] == h) {
            if (n == 0) n = 1;
            tap[tooth] = n;
        } /* if */
    } /* for */
    if (n != 0) n++;
} /* for */
```

The following program fragment adds data from the tap array into data stored in cumulative:

```
int tooth;
while (you want more bites) {
    bite;
    read L via the interface;
    create the tap array as shown above;
    /* add data to cumulative */
    for (tooth = 0; tooth < 8; tooth++)
        cumulative[tooth] [tap] [tooth]] ++;
} /* while */
```

The following program fragment displays the "slow motion" picture of a single bite:

```
int delay_unit; /* this is the delay in milliseconds
                   for one clock cycle in slow motion*/
int tooth, delay;
bite;
read the delay_unit;
read L and time via interface;
create the tap array as shown above;
display the teeth outline;
for (n = 1; n < 8; n++)
    delay = 0;
    for (tooth = 0; tooth < 8; tooth++) {
        if (tap[tooth] == n) {
            highlight the tooth to indicate a tap;
            delay = time [tooth];
        } /* if */
    } /* for */
    wait (delay * delay_unit);
} /* for */
```

Any of the above data arrays, e.g. tap, cumulative, can be displayed in part or entirely to communicate the data to the user. Other data arrays may also be produced, including arrays correlating the data to the jaw trajectory information delivered to the processor 400 by the jaw tracking device 406.

Figure 24:
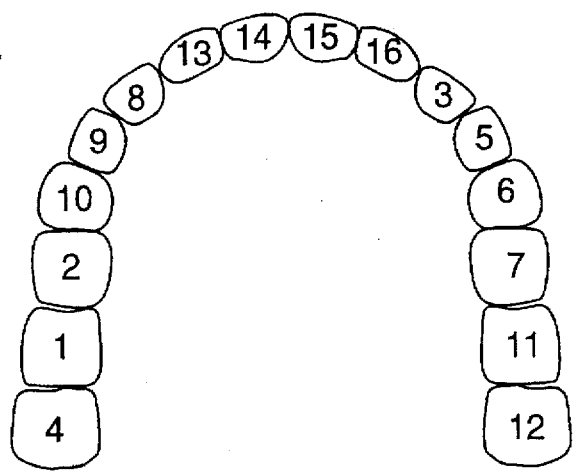
FIG. 24 is a display representing a patient's teeth, for example as displayed on the computer monitor of the FIG. 14 embodiment, overlaid with numbers indicating the sequence of tooth contact.
Figure 25:
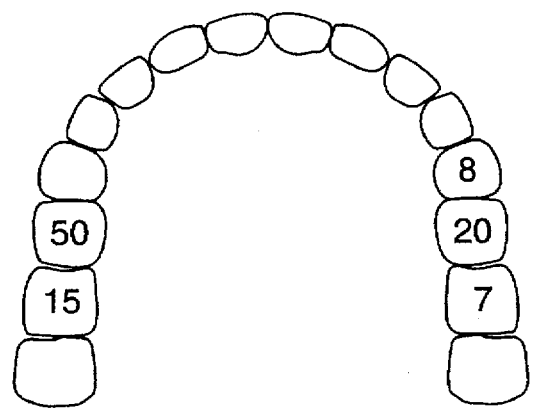
FIG. 25 is a display similar to that of FIG. 24 illustrating the percentage of times that certain teeth contact another tooth first (or in some other order) during plural contacts by a patient.
Figure 26:
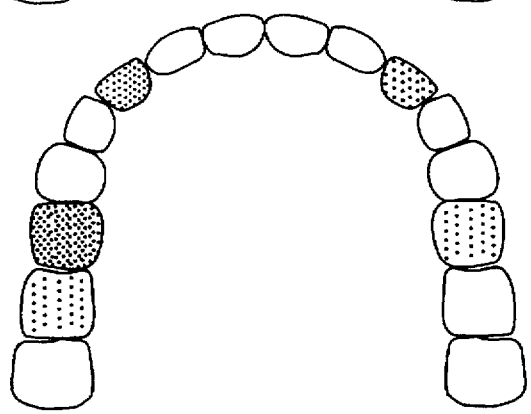
FIG. 26 is a display similar to that shown in FIG. 25 with teeth shaded to a different extent to indicate tooth contact information (for example the darkest tooth indicating more frequent first tooth contact).

FIGS. 24, 25 and 26 illustrate a variety of displays which may appear on monitor 402 from microprocessor 400 or which may be printed by printer 404, or both. The data may be presented in any other convenient form, as well. However, the illustrations of these figures make it easy for the dentist to evaluate the premature tooth contact information.

In particular, each of these displays detects a representation of teeth arranged in a horseshoe fashion as they would appear in the jaw of a patient.

In FIG. 24, the teeth are numbered to indicate the order in which the teeth made contact when a patient's jaw was tapped one time. This can be repeated any number of times to verify that the results are consistent. As can be readily seen in FIG. 24, the molars to the back of the left side of this figure hit first, and thus initial treatment or shaving of teeth could occur with these molars. As the progressive treatment takes place, these teeth will eventually not be the teeth which contact first and other teeth which are identified may then be treated. This process continues until a stable bite is achieved.

FIG. 25 illustrates an alternative manner of displaying the premature tooth contact information. In the FIG. 25 display, made after twenty jaw taps by a patient, numbers are overlayed on teeth to indicate the percentage of jaw taps or jaw closures in which the particular tooth was the first to contact another tooth. Again, it is readily apparent to a dentist which teeth require treatment.

FIG. 26 displays the data in yet another form utilizing shading to indicate the teeth which contact first. In this form, a cumulative density display format is utilized. Darker shading indicates frequent early contacts by a particular tooth during a plurality of jaw closings. White teeth would indicate no contact by a particular tooth of any tap. Dark black or the darker shading indicates frequent early contact, and lighter shadings indicate less frequent early contact. Instead of dark and light shading, colors may also be used and coded to correspond to the frequency of a particular tooth contacting first.

Figure 27:
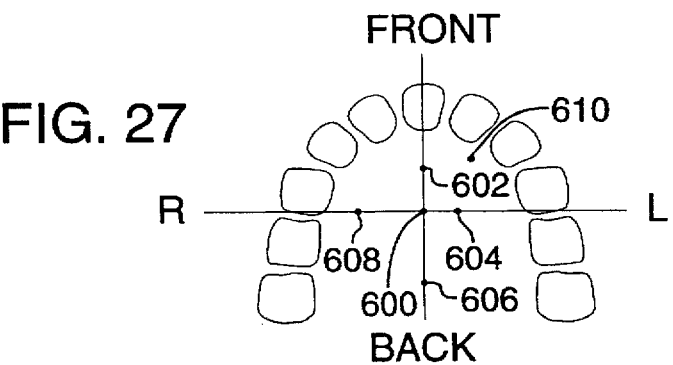
FIG. 27 is a display representing a jaw to illustrate a reference or coordinate system for jaw trajectory information.

FIG. 27 illustrates schematically teeth in the form of a dental arch and indicating a coordinate system on this arch. The origin 600 corresponds to a jaw trajectory which is centered in both the sagittal and frontal frames. The jaw tracking device 406 keeps track of a particular jaw trajectory relative to an origin, such as origin 600. In FIG. 27, for purposes of illustration, .602 indicates a trajectory which is forward in the sagittal plane, while .606 indicates a jaw trajectory which is rearward in the sagittal plane. In addition, .604 corresponds to a trajectory which is to the left in the frontal plane, while .608 corresponds to a trajectory which is to the right in the frontal plane. Furthermore, .610 corresponds to a jaw trajectory which is forward in the sagittal plane and to the left in the frontal plane, again, relative to the origin. Right and left in this figure refers to the position of the teeth in the patient's jaw looking up from the tongue toward the upper teeth. A jaw tracking device 406 in a conventional manner is able to map jaw trajectories in various directions relative to the origin.

Figure 28:
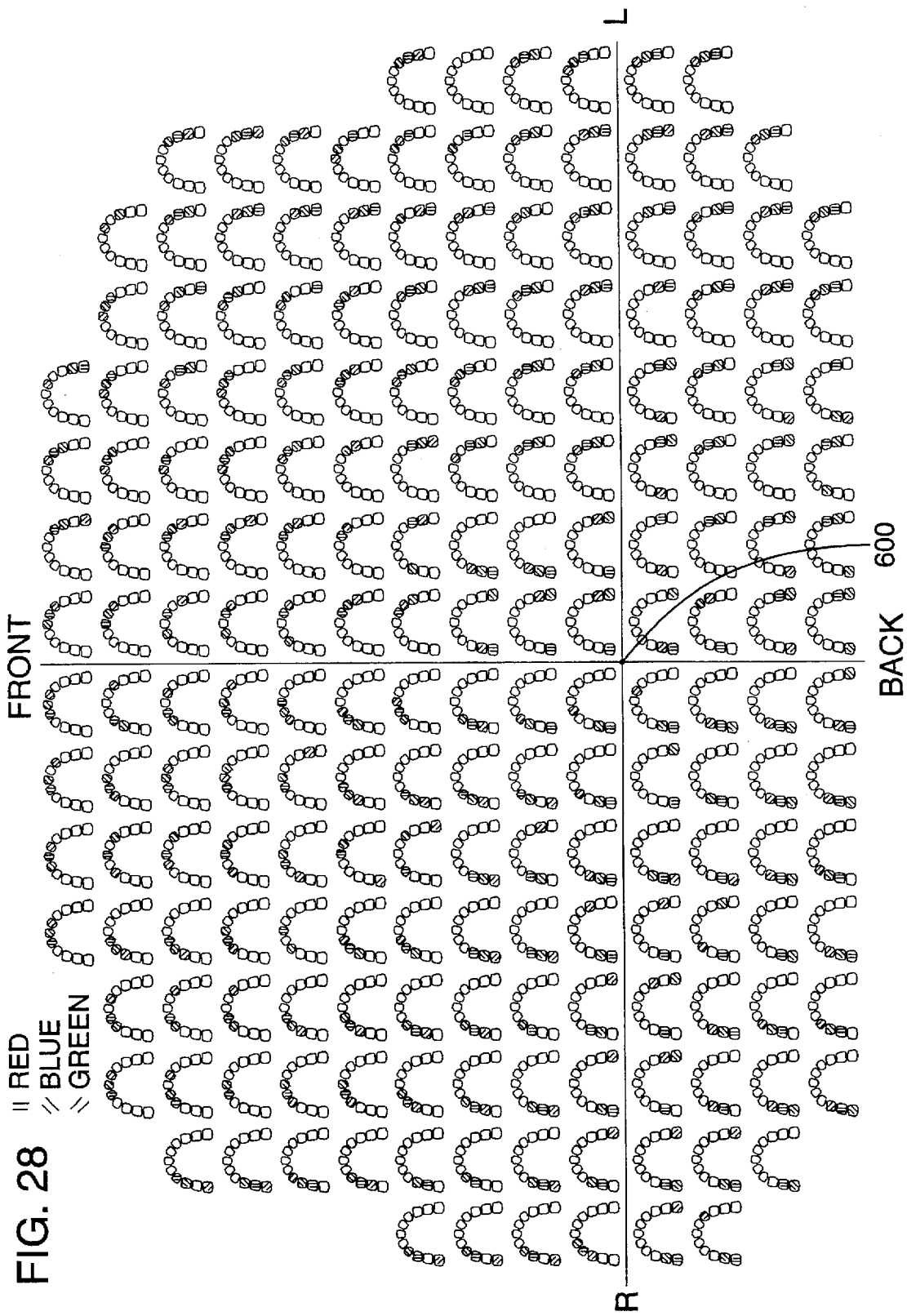
FIG. 28 is a representative display showing tooth contact information at various jaw trajectories in the sagittal and frontal planes.

FIG. 28 illustrates one form of display which may be used in providing a mapping of tooth contact variations with jaw trajectory as determined by the computer from the tooth contact data and jaw trajectory data.

In this figure, teeth marked with the code for the color red are the first to contact (typically an average of a number of jaw taps in each jaw trajectory is obtained). In addition, teeth marked with the code for the color blue are the second teeth to contact, while teeth marked with the code for the color green are the third teeth to contact. If a color monitor is used, the teeth are depicted with the respective colors.

In FIG. 28, the various depictions of the teeth shown in this figure correspond to jaw trajectories to the right, left, front and back at various positions relative to the origin.

In general, when a jaw closes along the anatomical midline (a midline trajectory recorded with the jaw tracking device), all the back teeth should make simultaneous contact. When the jaw closes on a trajectory that is shifted slightly to the right, all the back teeth on the right side should make contact. When the jaw closes on a trajectory that is further shifted to the right, all the back teeth and front teeth on the right side should make contact. Whatever the desired treatment, tooth contact for a particular patient may be achieved by continuing to treat the patient's teeth until this desired contact pattern is achieved at the various jaw trajectory positions.

In a typical procedure, when an average person (who has a relatively unstable bite) taps his or her teeth together, only two to four tooth contacts are typically made. Thus, two to four sensors produce outputs indicating tooth contact which may then be displayed. Tooth contacts that are consistently first and second can be identified by a dentist and shaved down, for example, with a drill. This procedure is called occlusal equilibration, enameloplasty or selective grinding. The tooth contact may be checked again, and the selective grinding continued, until tapping produces contacts on most or all of the teeth as nearly simultaneously as reasonably possible or desired. The simultaneity of tooth contact can be measured by, for example, recording and displaying the time between the first and the last of the tooth contacts registered during one closing of a jaw.

Figure 29:
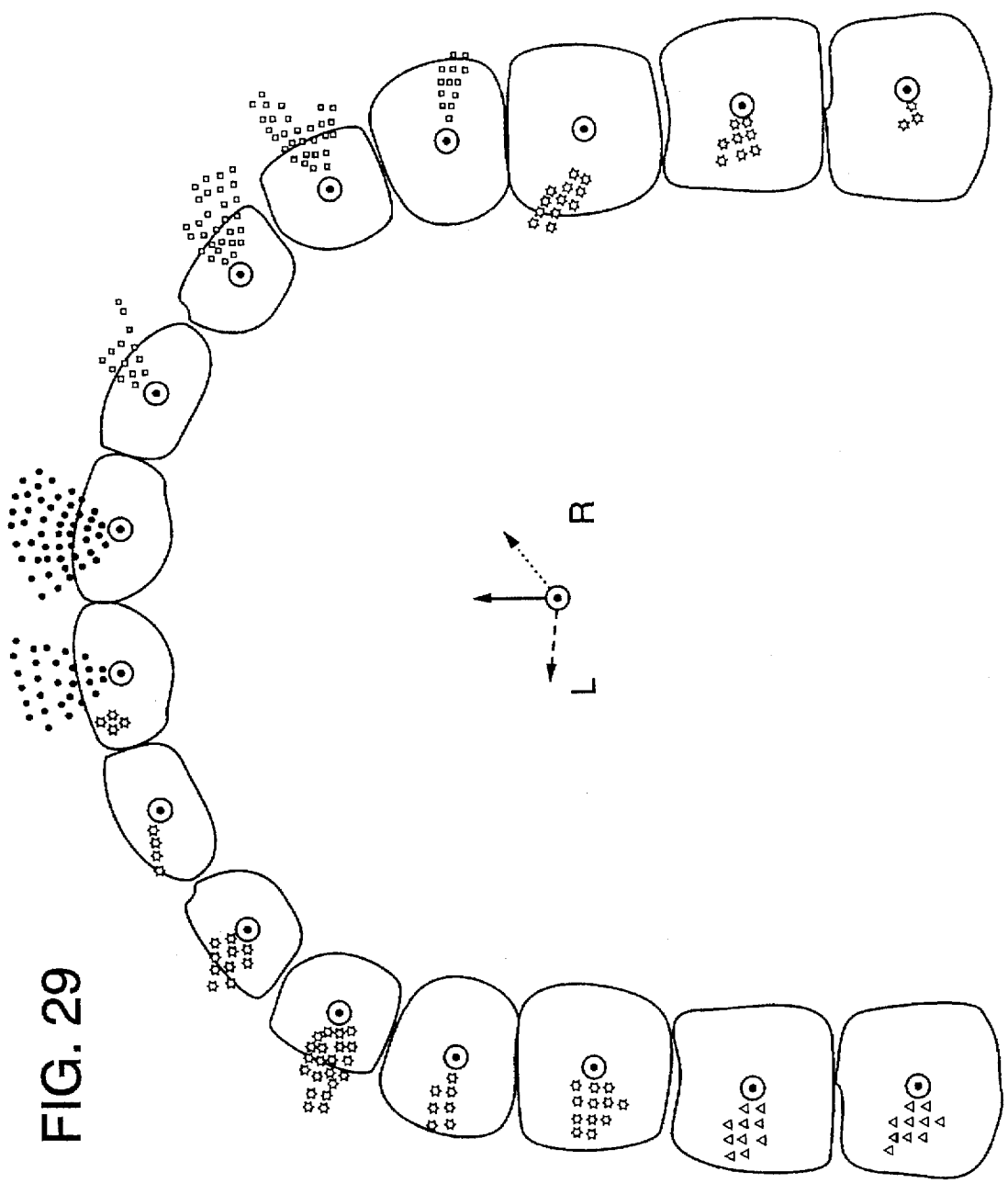
FIG. 29 illustrates another form of display usable in the present invention.

FIG. 29 illustrates another form of display which may be used in mapping the tooth contact variations which occur with various jaw trajectories to depict a full picture of the occlusal interface. This figure illustrates the lower arch of teeth, and the filled in spaces around the teeth illustrate the tooth contacts that occur when the lower jawbone moves in any direction and the teeth are tapped together. Marks indicated as * in this figure, for convenience in differentiating the marks from other jaw trajectories, and within the borders of the illustrated teeth signify contacts which take place during closure of the jaw in its habitual midline position (known as the intercuspal position). For the purposes of illustration, three directional movements of the lower jawbone are illustrated by the three arrows centered in the illustration (dashed arrow, solid line arrow and dotted arrow). If the jawbone moves to the left as the dashed arrow shoes, contacts occur fairly uniformly, as shown by the triangular shaped markings, on the left rear teeth (in a situation known as group function) and on the inside areas of some of the right rear teeth (in a situation known as balancing side contacts). If the jawbone moves straight ahead as in the solid line arrow, contact occurs only on the two front teeth, as shown by the solid dots. If the jawbone moves ahead and to the right (as the dashed arrow shows) contact occurs mainly on the right premolars, canine and lateral incisor, as shown by the square markings. Of course, in a color display, different colors may be used to indicate contacts associated with the respective jaw directions.

Having illustrated and described the principals of our invention with reference to several preferred embodiments, it should be apparent to those of ordinary skill in the art that the invention may be modified in arrangement and detail without departing from the inventive principles. We claim as our invention all such modifications as fall within the scope of the following claims.

What is claimed is:

1. An apparatus for determining the contact between at least one set of two teeth, each set of two teeth including an upper tooth and a lower tooth which contact one another at respective biting surfaces, the apparatus comprising:

a sensor for coupling to a surface of a first tooth of the set other than a biting surface;

the sensor producing an output signal upon contact of the two teeth of the set; and a signal processor coupled to the sensor so as to receive the output signal and operable to indicate the contact of two teeth of said at least one set in response to the output signal.

2. The apparatus of claim 1 wherein the sensor comprises a shock pulse or vibration sensor.

3. The apparatus of claim 1 wherein the sensor comprises an accelerometer.

4. The apparatus of claim 1 wherein the sensor comprises a piezoelectric shock pulse or vibration sensor.

5. The apparatus of claim 1 wherein the sensor is mounted to the upper tooth.

6. The apparatus of claim 1 in which the sensor is enclosed in a liquid impermeable sterilizable housing.

7. The apparatus of claim 1 including a sensor mounting bracket connected to the surface of a first tooth and in which the sensor is detachably mounted to the sensor mounting bracket.

8. The apparatus according to claim 1 in which the sensor is coupled to an exterior side surface of the upper molar of the set.

9. An apparatus according to claim 1 in which the signal processor comprises a signal processing circuit which includes a display which is operable to visually indicate the contact between the two teeth of the set.

10. The apparatus of claim 1 wherein the signal processor includes a signal processing circuit including a frequency-shaping circuit coupled to the sensor for shaping the output signal.

11. The apparatus of claim 10 wherein the signal processing circuit includes a threshold comparator for determining when the magnitude of the output signal or a derivative of the output signal exceeds a threshold magnitude.

12. The apparatus of claim 11 wherein the signal processing circuit includes an amplifier coupled to the filter.

13. The apparatus of claim 1 further comprising a second sensor coupled to a second tooth of a second set of two teeth, the second sensor producing a second output signal upon the contact of the two teeth of the second set, the signal processor being coupled to the second sensor so as to receive the second output signal, the signal processor circuit being responsive to the output signals to indicate which of the two sets of teeth are the first to contact.

14. The apparatus of claim 13 wherein the signal processor circuit is responsive to the output signals to indicate the sequence of contact of the two sets of teeth.

15. The apparatus of claim 14 in which the signal processor includes a visual display operable to visually indicate the sequence of contact of the two sets of teeth.

16. The apparatus of claim 1 including a plurality of sensors, each sensor being mounted to a respective tooth of an associated set of two teeth, there being plural sets of two teeth, each sensor producing an output signal upon contact of the teeth of the associated set, the signal processor being coupled to the plural sensors and being operable to process the output signals to indicate which set of teeth contact first.

17. The apparatus according to claim 16 in which the signal processor circuit is operable to process the output signals to indicate the sequence of contact of the sets of teeth.

18. The apparatus of claim 17 in which the signal processor includes a signal processing circuit with a plurality of storage devices for storing signals indicating the sequence of contact of the sets of teeth.

19. The apparatus of claim 18 in which the signal processing circuit includes a plurality of light emitting diodes to visually indicate the sequence of contact of the sets of teeth.

20. The apparatus of claim 16 in which the signal processor comprises a computer.

21. The apparatus of claim 20 which includes a jaw trajectory tracking apparatus coupled to the computer, the computer being programmed to correlate the output signal upon contact of two teeth with the jaw trajectory.

22. An apparatus for determining the contact of plural sets of teeth, each set including at least one upper tooth and at least one lower tooth, the apparatus comprising:

plural vibration sensors, each sensor for coupling to a tooth of an associated set of teeth and operable to produce an electrical output signal in response to the contact of the associated set of teeth; and a signal shaping circuit coupled to the plural sensors, the signal shaping circuit having plural signal shaping channels each signal shaping channel being coupled to an associated sensor and receiving the output signal from the associated sensor, each signal shaping channel including a frequency-shaping circuit, an amplifier and a threshold comparator, each signal shaping channel providing a shaped output signal at a first logic level in response to an input signal which corresponds to the associated sensor detecting contact of the associated set of teeth.

23. An apparatus according to claim 22 including a digital signal processing circuit comprising plural state indicating channels, each state indicating channel being coupled to a respective associated signal shaping channel, the digital signal processing circuit including at least one state storage circuit in each state indicating channel, said at least one state storage circuit storing a tooth contact indicating state in response to a shaped output signal at the first logic level from the associated signal shaping channel; and a visual display coupled to the digital signal processing circuit and operable to visually indicate the status of said at least one state storage circuit in a tooth contact indicating state.

24. An apparatus according to claim 23 in which each state indicating channel includes plural state storage circuits connected in series and responsive to a clock operating at a clock cycle, a first state storage circuit of a first state indicating channel being triggered to a tooth contact indicating state in response to a shaped output signal at the first logic level from an associated first signal shaping channel, the digital processing circuit being operable to maintain the status of the state storage circuits constant until a clock cycle occurs when a shaped output signal at the first logic level is present from another signal shaping channel, a first state storage circuit of another state indicating channel being triggered to a tooth contact indicating state in response to the shaped output signal at the first logic level from said another signal shaping channel, and the visual display being coupled to each of the state indicating channels and being operable to display the sequence of contact by the sets of teeth in response to the state of the state storage circuits.

25. An apparatus according to claim 24 including N sensors, wherein there are N state indicating channels and wherein the state storage circuits of each channel comprises a shift register including N bits, a first bit of the shift register of one state indicating channel being triggered to a tooth contact indicating state in response to the delivery of a shaped output signal at the first logic level to said one state indicating channel, the other bits of the shift register of said first state indicating channel being successively triggered to a tooth contact indicating state in response to the successive delivery of a shaped output signal at the first logic level to each of the other state indicating channels, and wherein the visual display comprises a matrix of light emitting diodes each coupled to a respective one bit of each of the shift register and indicating when the coupled shift register bit is in a tooth contact indicating state.

26. An apparatus for determining the contact of biting surfaces of plural sets of teeth, each set including at least one upper tooth and at least one lower tooth, the apparatus comprising: plural vibration sensors, each for coupling to a surface of a tooth which does not contact another tooth during biting and operable to produce an output signal in response to contact between the tooth to which the sensor is coupled and another tooth; and a signal processor responsive to the output signals to determine tooth contact.

27. A method for detecting tooth contact comprising:

providing a sensor for coupling to a first tooth at a position on the first tooth that does not come in contact with another tooth during biting;

sensing vibration from the contact of the first tooth to another tooth during biting;

converting the vibration from the contact of the first tooth to a first electrical signal; and processing the first electrical signal to determine when the first tooth makes contact with another tooth.

28. The method of claim 27 wherein the method further includes:

providing a second sensor for coupling to a second tooth at a position on the second tooth that does not come in contact with another tooth during biting;

sensing vibration from the contact of the second tooth to another tooth during biting;

converting the vibration from the contact of the second tooth to a second electrical signal; and processing the second electrical signal to determine when the second tooth makes contact with another tooth.

29. The method of claim 28 further including:

transferring the first and second electrical signals to an output device to visually display when the first tooth makes contact relative to the contact of the second tooth.

30. A method of determining the contact between at least two teeth comprising:

detecting vibration occurring when the at least two teeth contact; and indicating, from an electrical signal corresponding to the detected vibration, the contact of the two teeth.

31. A method according to claim 30 of detecting contact between plural sets of teeth wherein the indicating step comprises the step of indicating the first set of teeth to contact.

32. A method according to claim 30 of detecting contact between plural sets of teeth in which the indicating step comprises the step of indicating the sequence in which at least certain of the plural sets of teeth contact.

33. A method according to claim 30 in which the indicating step comprises the step of visually indicating the first set of teeth to contact.

34. A method according to claim 30 in which the indicating step comprises the step of visually indicating the sequence in which the plural sets of teeth contact.

35. A method determining the contact between at least one set of two teeth, the two teeth contacting at biting surfaces thereof, the method comprising:

mounting a sensor to at least one of the teeth at a surface other than the biting surface;

processing a signal from the sensor in response to contact between the two teeth; and displaying a visual indication of contact between the two teeth in response to the processed signal corresponding to contact between the two teeth.

36. A method according to claim 35 for determining the contact between plural sets of two teeth, each set of teeth contacting at respective biting surfaces thereof, the method comprising:

mounting a respective sensor to at least one of the teeth of each set at a surface other than the biting surface;

processing signals from the sensors in response to contact between the teeth of the sets of teeth; and displaying a visual indication of the first set of teeth to contact.

37. A method according to claim 36 in which the displaying step comprises the step of displaying the sequence at which of the sets of teeth contact.

38. A sensor support comprising:

a sensor carrier; and plural tooth contact sensors coupled to the sensor carrier adjacent to outer side surfaces of teeth when the sensor carrier is inserted into a person's mouth.

39. A sensor support according to claim 38 in which the sensor carrier includes a body portion having a tooth engaging surface conforming to the shape of the outer side surfaces of teeth of an arch of an individual whose teeth are to be evaluated for tooth contact.

40. A sensor support according to claim 39 including an arch shaped reinforcing element within the body portion, the body portion including plural apertures each positioned to receive a respective sensor.

41. A sensor support according to claim 38 in which the sensors are slidably coupled to the sensor carrier so as to be slidable into respective positions adjacent to the outer surfaces of teeth to be monitored for tooth contacts.

42. A sensor support according to claim 41 in which the sensor carrier comprises first and second bite fork arms.

43. A sensor support according to claim 42 in which the first and second bite fork arms are pivoted together for pivoting about a first axis.

44. A sensor support according to claim 41 in which the sensor carrier comprises an arch having arms projecting forwardly from a rear portion of the arch, each arm being positioned at a respective side of a patient's mouth and wherein the sensors are slidably coupled to the arms.

45. A sensor support according to claim 38 including means for dampening the passage of vibration between the respective sensors.

46. A sensor support according to claim 38 in which the sensors are each biased against a respective tooth.

47. A sensor support according to claim 38 in which the sensor carrier is arch shaped and is comprised of a wire.

\* \* \* \* \*